United States Patent
Osorio

(10) Patent No.: US 10,321,841 B2
(45) Date of Patent: Jun. 18, 2019

(54) QUANTITATIVE MULTIVARIATE ANALYSIS OF SEIZURES

(75) Inventor: Ivan Osorio, Leawood, KS (US)

(73) Assignee: FLINT HILLS SCIENTIFIC, LLC, Lawrence, KS (US)

( * ) Notice: Subject to any disclaimer, the term of this patent is extended or adjusted under 35 U.S.C. 154(b) by 224 days.

(21) Appl. No.: 13/116,873

(22) Filed: May 26, 2011

(65) Prior Publication Data

US 2011/0295332 A1    Dec. 1, 2011

Related U.S. Application Data

(60) Provisional application No. 61/348,674, filed on May 26, 2010.

(51) Int. Cl.
| | |
|---|---|
| A61N 1/36 | (2006.01) |
| A61B 5/0476 | (2006.01) |
| A61B 5/00 | (2006.01) |
| G16H 50/20 | (2018.01) |
| G06F 19/00 | (2018.01) |

(52) U.S. Cl.
CPC .......... *A61B 5/0476* (2013.01); *A61B 5/4094* (2013.01); *A61B 5/4833* (2013.01); *A61N 1/36064* (2013.01); *A61N 1/36139* (2013.01); *G06F 19/00* (2013.01); *G16H 50/20* (2018.01)

(58) Field of Classification Search
CPC ................................................. A61N 1/36064
USPC ................................... 600/544, 545; 607/45
See application file for complete search history.

(56) References Cited

U.S. PATENT DOCUMENTS

| | | | | |
|---|---|---|---|---|
| 3,863,625 A | * | 2/1975 | Viglione et al. | 600/545 |
| 5,857,978 A | * | 1/1999 | Hively et al. | 600/544 |
| 5,995,868 A | * | 11/1999 | Dorfmeister | A61B 5/048 |
| | | | | 600/300 |

(Continued)

FOREIGN PATENT DOCUMENTS

WO    2009103156 A1    8/2009

OTHER PUBLICATIONS

Ivan Osorio, et al.; Automated Seizure Abatement in Humans Using Electrical Stimulation; 2005 American Neurological Association; pp. 258-268; Published online Jan. 26, 2005 in Wiley InterScience (www.interscience.wiley.com).

(Continued)

*Primary Examiner* — Allen Porter
(74) *Attorney, Agent, or Firm* — CF3; Stephen Eisenmann

(57) ABSTRACT

Methods, including a method, comprising selecting a plurality of dependent variables relating to each of a plurality of seizures in a patient; selecting a plurality of independent variables, wherein each independent variable comprises a therapy parameter, a therapy delivery parameter, a temporal factor, an environmental factor, or a patient factor; quantifying at least one relationship between each of at least two dependent variables and each of at least two independent variables; and performing an action in response to said quantifying, selected from reporting said at least one relationship, assessing an efficacy of a therapy, assessing an adverse effect of said therapy, providing a therapy modification recommendation, or adjusting said therapy. A medical device system capable of implementing a method. A non-transitory computer readable program storage medium containing instructions that, when executed by a computer, perform a method.

19 Claims, 11 Drawing Sheets

(56) References Cited

U.S. PATENT DOCUMENTS

| | | | |
|---|---|---|---|
| 6,304,775 B1 * | 10/2001 | Iasemidis et al. | 600/544 |
| 6,507,754 B2 * | 1/2003 | Le Van Quyen et al. | 600/544 |
| 6,594,524 B2 * | 7/2003 | Esteller et al. | 607/45 |
| 6,658,287 B1 * | 12/2003 | Litt et al. | 600/544 |
| 6,678,548 B1 * | 1/2004 | Echauz | A61B 5/0476 600/544 |
| 2001/0003799 A1 * | 6/2001 | Boveja | A61N 1/0536 607/45 |
| 2003/0083716 A1 * | 5/2003 | Nicolelis | A61N 1/36064 607/45 |
| 2003/0158587 A1 * | 8/2003 | Esteller et al. | 607/45 |
| 2004/0068199 A1 * | 4/2004 | Echauz et al. | 600/544 |
| 2004/0133119 A1 * | 7/2004 | Osorio et al. | 600/544 |
| 2004/0138536 A1 | 7/2004 | Frei et al. | |
| 2004/0138580 A1 * | 7/2004 | Frei et al. | 600/544 |
| 2006/0129202 A1 * | 6/2006 | Armstrong | 607/45 |
| 2007/0213785 A1 * | 9/2007 | Osorio et al. | 607/45 |
| 2007/0287931 A1 | 12/2007 | Dilorenzo | |
| 2008/0103532 A1 * | 5/2008 | Armstrong | A61N 1/3605 607/2 |
| 2009/0069863 A1 * | 3/2009 | Pless et al. | 607/45 |
| 2009/0082640 A1 | 3/2009 | Kovach et al. | |

OTHER PUBLICATIONS

Ivan Osorio; et al.; Toward a Quantitative Multivariate Analysis of the Efficacy of Antiseizure Therapies; Epilepsy and Behavior 18 (2010) pp. 335-343.

PCT Search Report for PCT/US2011/038158; dated Aug. 23, 2011; 7 pgs.

* cited by examiner

| Independent Variable ID (e.g., Electrical Stimulation Current Amplitude) | | |
|---|---|---|
| Dependent Variable | Immediate Effect | Carryover Effect |
| Seizure Intensity | +0.4 | -0.1 |
| Seizure Duration | -0.2 | +0.2 |
| Extent of Seizure Spread | -0.3 | -0.01 |
| Inter-Seizure Interval | N/A | +0.6 |
| Seizure Severity | -0.1 | +0.09 |

+ = Beneficial
- = Detrimental

FIGURE 6

QUANTITATIVE MULTIVARIATE ANALYSIS OF SEIZURES

BACKGROUND OF THE DISCLOSURE

The present application claims priority from co-pending U.S. patent application 61/348,674, filed May 26, 2010, the disclosure of which is hereby incorporated by reference in its entirety.

1. Field of the Disclosure

The present disclosure relates generally to the field of epilepsy. More particularly, it concerns analysis of seizures to quantify effects of one or more independent variables on one or more seizure dependent variables.

SUMMARY OF THE DISCLOSURE

In one embodiment, the present disclosure relates to a medical device system, comprising: a data acquisition unit configured to acquire data relating to a plurality of dependent variables relating to each of a plurality of seizures in a patient and data relating to a plurality of independent variables, wherein each of said independent variables comprises a therapy parameter, a therapy delivery parameter, a temporal factor, an environmental factor, or a patient factor; a data quantification unit configured to quantify at least one relationship between at least two of said dependent variables and at least two of said independent variables; and a responsive action unit configured to perform an action in response to said quantifying, wherein said action is selected from reporting said at least one relationship, assessing an efficacy of a therapy, assessing an adverse effect of said therapy, providing a therapy modification recommendation, or adjusting said therapy.

In one embodiment, the present disclosure relates to a method of assessing an efficacy of an epilepsy therapy, comprising: selecting a plurality of dependent variables relating to each of a plurality of seizures in a patient; selecting a plurality of independent variables, wherein each independent variable comprises a therapy parameter, a therapy delivery parameter, a temporal factor, an environmental factor, or a patient factor; quantifying at least one relationship between each of at least two dependent variables and each of at least two independent variables; and performing an action in response to said quantifying, selected from reporting said at least one relationship, assessing an efficacy of a therapy, assessing an adverse effect of said therapy, providing a therapy modification recommendation, or adjusting said therapy.

In one embodiment, the present disclosure relates to a non-transitory computer readable program storage medium containing instructions that, when executed by a computer, perform a method disclosed herein.

BRIEF DESCRIPTION OF THE DRAWINGS

The disclosure may be understood by reference to the following description taken in conjunction with the accompanying drawings, in which like reference numerals identify like elements, and in which:

FIG. 6 depicts another exemplary output of a model unit, in accordance with one illustrative embodiment of the present disclosure;

Figure 1:
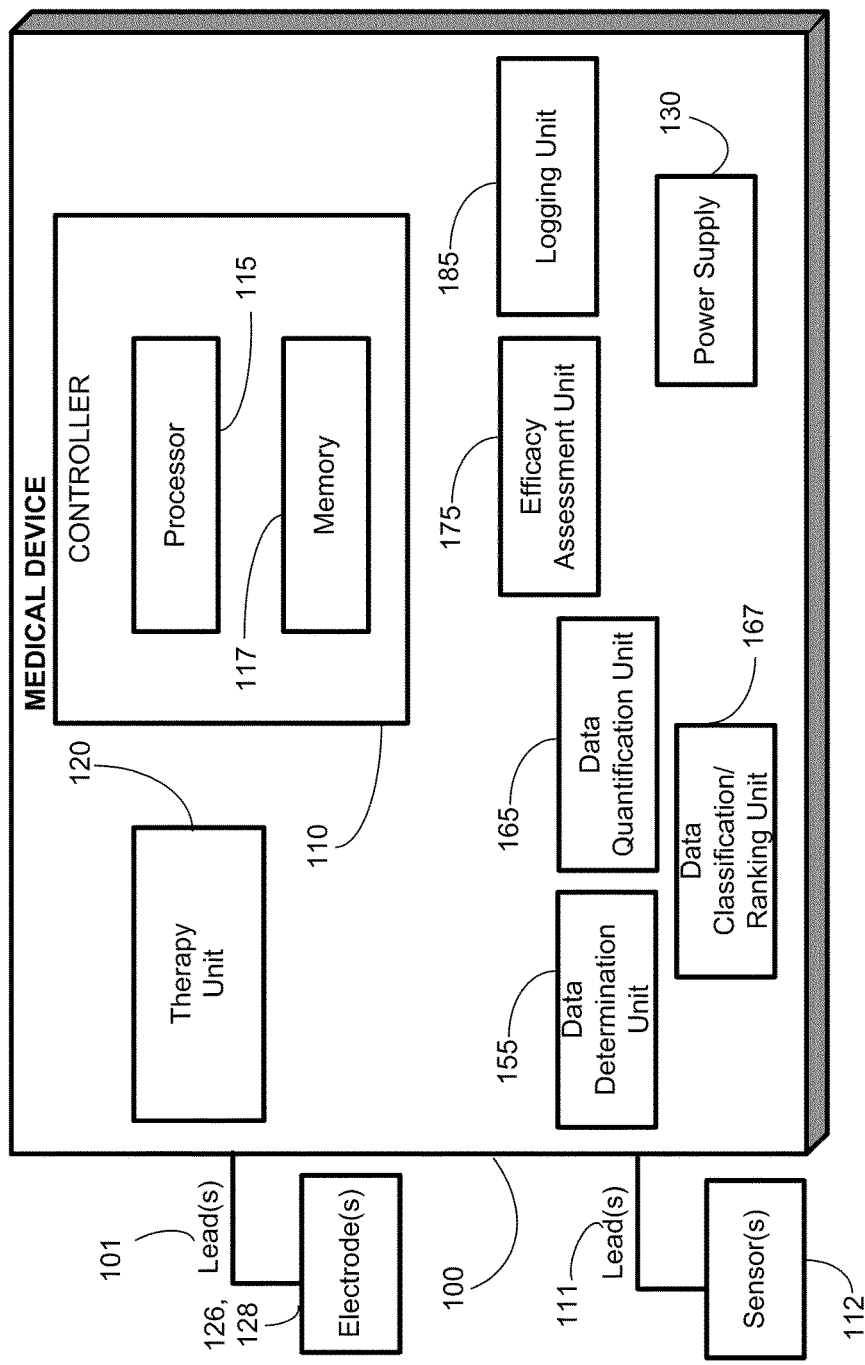
FIG. 1 provides a block diagram of a medical device system, in accordance with one illustrative embodiment of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the appended claims.

DESCRIPTION OF ILLUSTRATIVE EMBODIMENTS

Illustrative embodiments of the disclosure are described herein. Not all features of an actual implementation are described. In the development of any actual embodiment, numerous implementation-specific decisions must be made to achieve the design-specific goals, which will vary from one implementation to another. While possibly complex and time-consuming, such a development effort would nevertheless be a routine undertaking for persons of ordinary skill in the art having the benefit of this disclosure.

This document does not intend to distinguish between components that differ in name but not function. The terms "including" and "includes" are used in an open-ended fashion, and should be interpreted to mean "including, but not limited to." "Couple" or "couples" is intended to mean either a direct or an indirect electrical connection. "Direct contact," "direct attachment," or providing a "direct coupling" indicates that a surface of a first element contacts the surface of a second element with no substantial attenuating medium there between, but are not intended to exclude the presence of small quantities of substances, such as bodily fluids, that do not substantially attenuate electrical connections. The word "or" is used in the inclusive sense (i.e., "and/or") unless a specific use to the contrary is explicitly stated.

"Electrode" or "electrodes" may refer to one or more stimulation electrodes (i.e., electrodes for delivering a therapeutic signal generated by a medical device to a tissue), sensing electrodes (i.e., electrodes for sensing a physiological indication of a state of a patient's body), and/or electrodes that are capable of both signal sensing and therapy delivery.

Turning to FIG. 1, a block diagram depiction of a medical device 100 is provided, in accordance with one illustrative embodiment of the present disclosure. In some embodiments, the medical device 100 may be implantable, while in other embodiments the medical device 100 may be completely external to the body of the patient, while in still other embodiments, some of its units may be implanted and others may be external.

Medical device 100 may comprise a controller 110 capable of controlling various aspects of the operation of the medical device 100. The controller 110 may be capable of receiving internal data or external data, and in one embodiment, may be capable of causing a therapy unit 120 to deliver a therapy for epilepsy to a patient's body or a part thereof. Generally, the controller 110 may be capable of affecting substantially all functions of the medical device 100.

The controller 110 may comprise various components, such as a processor 115, a memory 117, etc. The processor 115 may comprise one or more microcontrollers, microprocessors, etc., capable of performing various executions of software components. The memory 117 may comprise various memory portions where a number of types of data (e.g., internal data, external data instructions, software codes, status data, diagnostic data, etc.) may be stored. The memory 117 may comprise one or more of random access memory (RAM), dynamic random access memory (DRAM), electrically erasable programmable read-only memory (EEPROM), flash memory, etc.

The medical device 100 may also comprise a power supply 130. The power supply 130 may comprise a battery, voltage regulators, capacitors, etc., to provide power for the operation of the medical device 100. Power supply 130 may comprise a power source that in some embodiments may be rechargeable. In other embodiments, a non-rechargeable power source may be used. Power supply 130 may comprise a lithium/thionyl chloride cell or a lithium/carbon monofluoride (LiCFx) cell if the medical device 100 is implantable, or may comprise conventional watch or 9V batteries for external (i.e., non-implantable) embodiments. Other battery types may also be used.

The medical device system depicted in FIG. 1 may also comprise one or more sensor(s) 112. In the depicted embodiment, the sensor(s) 112 are coupled via sensor lead(s) 111 to the medical device 100. In other embodiments, the sensor(s) 112 can be in wireless communication with the medical device 100. Sensor(s) 112 are capable of receiving signals related to a body parameter, such as the patient's brain activity (e.g., electrical, chemical, cognitive), heart activity, blood pressure, and/or temperature, among others, and delivering the signals to the medical device 100. The sensor(s) 112 may also be capable of detecting a kinetic signal associated with a patient's movement. The sensor(s) 112, in one embodiment, may be an accelerometer. The sensor(s) 112, in another embodiment, may be an inclinometer. In another embodiment, the sensor(s) 112 may be an actigraph or a gyroscope. In one embodiment, the sensor(s) 112 may be implanted in the patient's body. In other embodiments, the sensor(s) 112 are external structures that may be placed on the patient's skin, such as over the patient's heart or elsewhere on the patient's torso or limbs or on the scalp or brain. The sensor(s) 112, in one embodiment, may be a multimodal signal sensor capable of detecting various body signals, including cardiac signals associated with the patient's cardiac activity and kinetic signals associated with the patient's movement.

Alternatively or in addition, in one embodiment, the sensor(s) 112 may be configured to detect signals associated with electrical activity of the patient's brain. For example, the sensor(s) 112 may be electroencephalography (EEG) sensors or electocorticography (ECoG) sensors.

In other embodiments, a separate responsiveness and/or awareness unit may be provided as part of the medical device or as a separate unit.

In addition or alternatively to body signals relating to dependent variables, the sensor(s) 112 may be configured to detect signals relating to independent variables. Such sensor(s) 112 may sense body signals (e.g., a wake/sleep sensor) or non-body signals (e.g., a clock to sense time of day or other temporal factor(s)).

It should be borne in mind the sensor(s) 112 are optional, and need not be present in every embodiment in accordance with the present disclosure.

The data determination unit 155 may be configured to determine at least one dependent variable relating to each of a plurality of seizures in a patient. In one embodiment, the at least one dependent variable may be based at least in part on at least one body signal, such as a body signal detected by sensor(s) 112. Alternatively or in addition, the data determination unit 155 may determine dependent variables based on signals acquired by an external source (not shown) and communicated by the external source to the data acquisition unit 155. Where a therapy is provided to treat a seizure, the dependent variables may provide an indication of the effect of the therapy in some embodiments. For example, the dependent variables may identify whether the direction of the effect of the therapy is positive, negative, or substantially neutral, and/or the magnitude of the effect. "Substantially neutral" here means being neutral within dead band error and/or the detection limits of the system.

Any dependent variable(s) relating to seizures may be determined by the data acquisition unit 155. In one embodiment, the at least one dependent variable may be selected from intensity of the seizure, duration of the seizure, extent of spread of the seizure, seizure severity index, an adverse effect (e.g., intolerability or lack of safety) of a therapy, and time elapsed between a seizure and the next seizure(s) or between a seizure and previous seizures, referred to herein as inter-seizure intervals. Inter-seizure interval may be determined by computing the time elapsed between the onset of two or more seizures or between the end of a seizure and the onset of the next. The seizure severity index may comprise one or more of an autonomic index, a neurologic index, a metabolic index, a respiratory index, a tissue stress marker, a musculoskeletal index, or an endocrine index. Other dependent variables include, but are not limited to, efficacy of a therapy, side effects of a therapy, and tolerability of a therapy.

In an embodiment wherein the at least one dependent variable may be based at least in part on at least one body signal, an intensity of a seizure may be determined from a peak heart rate above a reference interictal heart rate or an area under the curve of heart rate elevation above a reference interictal heart rate, among other body signals and/or values calculable from body signals. A duration of a seizure may be determined from a duration of a heart rate elevation above a reference interictal heart rate, among other sources. A heart rate elevation above a reference interictal heart rate, among other sources, may also be used to determine a time elapsed between seizures (e.g., most recent seizure and the next seizure). An extent of spread of a seizure may be determined from kinetic signals indicative of movement of various limbs or signals relating to the patient's responsiveness or awareness, from the number of organs or functions affected by a seizure (e.g., brain, heart, breathing, metabolic, etc.).

More information regarding detection of epileptic events and determination of severity and location in the body of epileptic events can be found in U.S. patent application Ser. No. 12/756,065, filed Apr. 7, 2010; U.S. patent application Ser. No. 12/770,562, filed Apr. 29, 2010; U.S. patent application Ser. No. 12/896,525, filed Oct. 1, 2010; U.S. patent application Ser. No. 13/040,996, filed Mar. 4, 2011; U.S. patent application Ser. No. 13/091,033, filed Apr. 20, 2011; and U.S. patent application Ser. No. 13/098,262, filed Apr. 29, 2011; all of which are hereby incorporated herein by reference in their entirety.

Any or all of these dependent variables may also be determined from EEG or ECoG of the patient's brain or from cognitive activity.

The intensity of the seizure, the duration of the seizure, and the extent of spread of the seizure, may be taken together to yield a metric of seizure severity, e.g., a seizure severity index. Seizure severity thus may be based on at least one of the dependent variables referred to above. In one embodiment, seizure severity may be defined as one-third of the sum of the standardized natural log of intensity of the seizure, the standardized natural log of duration of the seizure, and the standardized natural log of extent of spread of the seizure. In another embodiment, seizure severity may be expressed as the sum of at least one of intensity or duration of change from baseline activity in each organ or function impacted by the seizure, multiplied by the total number of organs or functions impacted by the seizure.

The data quantification unit 165 may be capable of quantifying at least one relationship between at least one of the plurality of dependent variables and at least one of the plurality of independent variables. In one embodiment, the at least one independent variable may be selected from whether the seizure was treated with at least one therapy, whether the previous seizure was treated with at least one therapy, the type of therapy, the drug/chemical dose, current density in an electrical therapy, or degree of temperature change induced by a thermal therapy, the target of the therapy, a time elapsed since a previous treatment with at least one therapy, a number of seizures since a previous treatment with at least one therapy, a time of day the seizure occurred, a time of the month (or year) the seizure occurred, the level of consciousness of the patient (e.g., awake vs. asleep); the level and type of cognitive activity, the patient's health state, or two or more thereof.

In one embodiment, each independent variable may comprise a therapy parameter, a therapy delivery parameter, a temporal factor, an environmental factor, or a patient factor.

The data quantification unit 165 may be capable of quantifying using any mathematical technique. In one embodiment, quantifying may comprise any form of regression analysis or models on said at least one dependent variable and said at least one independent variable. In another embodiment, any form of analyses or modeling applicable to multivariate situations or phenomena of efficacy of therapy as a function of type of therapy, (e.g., drug, electrical stimulation), one or more parameters defining the therapy (e.g., dose or quantity, duration or frequency of said therapy, current, pulse width, on time, off time), the number of different therapies being delivered, the delivery modality (e.g., continuous, contingent, periodic or randomly-timed), the time of day, month, season, or year of delivery, the anatomical target of the therapy, the conditions of a patient during delivery (e.g., awake or asleep, cognitively active or inactive, physically active or inactive, healthy or ill, fasting or non-fasting, ingestion of alcohol or of psychoactive drugs, duration and type of light exposure, stress level, psychiatric/emotional state, menses, ovulation or pregnancy in the case of women among other independent variables).

In yet another embodiment, regression analyses of any form or any other type of suitable analyses may applied to assessing adverse effects of a therapy as a function of type of therapy, the dose or quantity, duration or frequency of said therapy, the number of different therapies being delivered, the delivery modality (e.g., continuous, contingent, periodic or randomly-timed), the time of day, month or year of delivery, the anatomical target of the therapy, the conditions of a patient during delivery (e.g., awake or asleep, cognitively active or inactive, physically active or inactive, healthy or ill, fasting or non-fasting, ingestion of alcohol or of psychoactive drugs, duration and type of light exposure, stress level, psychiatric/emotional state, menses, ovulation or pregnancy in the case of women among others).

The data quantification unit 165 may be capable of quantifying any of a number of effects of an independent variable on a dependent variable. In one embodiment, the at least one effect may be the presence of serial correlation between dependent variables. In other words, the at least one effect may be the extent to which seizure intensity, seizure duration, extent of seizure spread, and/or time elapsed between seizures depends on previous seizures. In another embodiment, in which treatment with at least one therapy may be performed, the effect may be an immediate result of the treatment. "Immediate" in this context refers to the period of time encompassed by the delivery of a therapy (for electrical and thermal modalities) or the half-life of a drug in tissue or serum (for a drug or chemical modality). In another embodiment, in which treatment with at least one therapy may be performed, the effect may outlast the time encompassed by the delivery of a therapy, also referred to as a "carry-over" effect.

In other embodiments, in which treatment with at least one therapy may be performed, one or more longer-time scales, including but not limited to an entire period for which data is available, may be considered.

The relationships quantified in embodiments of this disclosure may relate to individual seizures, groups of seizures, or all seizures for which data is available.

In another embodiment (not shown), the medical device 100 may comprise a data quantification/qualification unit, which may be capable of quantifying one or more relationships, as discussed above, and may alternatively or in addition be capable of qualifying one or more relationships.

The data classification/ranking unit 167 may be capable of performing a further classification or ranking of a plurality of independent variables, a plurality of dependent variables, or both on a quantification of a relationship determined by the data quantification unit 165. The data classification/ranking unit 167 is optional and need not be present in every embodiment according to the present disclosure. The therapy unit 120 may be capable of administering at least one therapy to a patient. Any therapy may be administered. In one embodiment, the at least one therapy may be selected from an electrical stimulation of a target structure of the brain, an electrical stimulation of a target portion of a cranial nerve, a drug, a thermal treatment of a target portion of a neural structure, a noxious or non-noxious sensory therapy to a sensory organ (e.g., eyes, ears, nose, mouth, skin pressure sensors, skin pain sensors, etc.), a cognitive therapy to the patient, or two or more thereof. In a particular embodiment, the at least one therapy may be an electrical stimulation to the brain, a cranial nerve, or both of the patient. Cognitive (e.g., "biofeedback") therapies may be also administered.

The target structure of the brain may, but need not, be the entire brain. The target portion of the cranial nerve may by the entire cranial nerve, but need not be. The target portion of the neural structure may by the entire neural structure, but need not be.

More information regarding exemplary embodiments of electrical stimulation of a cranial nerve may be found in U.S. Pat. Nos. 4,702,254, 4,867,164, and 5,025,807 to Dr. Jacob Zabara, and in U.S. Pat. Nos. 6,961,618 and 7,457,665 to Ivan Osorio and Mark G. Frei, all of which are hereby incorporated by reference in their entirety.

It should be borne in mind the therapy unit 120 is optional, and need not be present in every embodiment in accordance with the present disclosure.

The efficacy assessment unit 175 may be capable of assessing a magnitude of efficacy of at least one therapy. In one embodiment, the efficacy assessment unit 175 may take as an input a quantified effect from the data quantification unit 165 and determine an efficacy based at least in part on the quantified effect. For example, if the data quantification unit 165 quantifies a reduction in seizure severity for treated seizures and no change in seizure severity for untreated seizures, the efficacy assessment unit 175 may return a result indicating the treatment may be considered efficacious. In one embodiment, the efficacy assessment unit 175 may quantify the efficacy as part of the assessment.

The efficacy assessment unit 175 may be capable of determining if the effect is positive (beneficial), negative (detrimental) or neutral (no effect) on at least one of a seizure intensity, duration, extent of spread, seizure severity index, or inter-seizure interval length(s).

The efficacy assessment unit 175 may be capable of ranking (e.g. from highest to lowest) and classifying as positive, negative or neutral, the effect of a therapy on at least one of a seizure intensity, duration, extent of spread or inter-seizure interval length(s).

In one embodiment, the efficacy assessment unit 175 may be considered a responsive action unit.

It should be borne in mind the efficacy assessment unit 175 is optional, and need not be present in every embodiment in accordance with the present disclosure.

The logging unit 185 may be capable of storing and/or reporting one or more values determined by the data determination unit 155, the data quantification unit 165, the efficacy assessment unit 175, the therapy unit 120, or two or more thereof. In one embodiment, the logging unit 185 may be considered a responsive action unit. The logging unit 185 is optional, and need not be present in every embodiment in accordance with the present disclosure.

In one embodiment, one or more responsive actions may be performed manually. Alternatively or in addition, one or more responsive actions may be performed automatically.

One or more of the blocks illustrated in the block diagram of the medical device 100 in FIG. 1 may comprise hardware units, software units, firmware units, or any combination thereof. Additionally, one or more blocks illustrated in FIG. 1 may be combined with other blocks, which may represent circuit hardware units, software algorithms, etc. Additionally, any number of the circuitry or software units associated with the various blocks illustrated in FIG. 1 may be combined into a programmable device, such as a field programmable gate array, an ASIC device, etc.

In on embodiment of the present disclosure, principal component analysis or a similar/related analysis may be performed to determine the number of components (e.g., dependent variables), subject to variability of the data (e.g., seizure intensity, duration, or extent of spread) as a function of at least one of the therapy independent variables.

Figure 2:
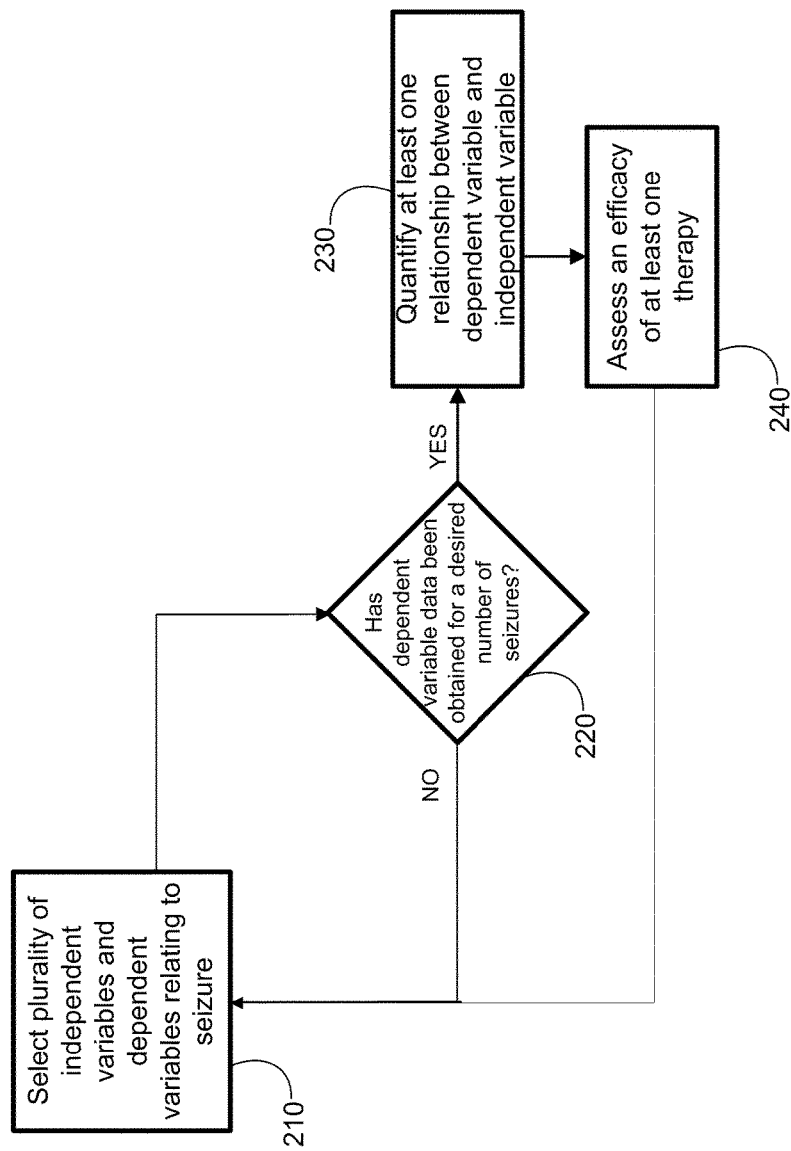
FIG. 2 shows a flowchart of an implementation of a method, in accordance with one illustrative embodiment of the present disclosure.

FIG. 2 shows a flowchart of an implementation of a method. Selection of a plurality of dependent variables relating to a seizure in a patient may be performed at 210. The plurality of dependent variables may be selected from intensity of the seizure, duration of the seizure, extent of spread of the seizure, seizure severity index, a seizure frequency, an adverse effect of a therapy, and the inter-seizure interval(s), referred to in the Example below as "Time Between Seizures" (TBS). In one embodiment, the plurality of dependent variables is selected from inter-seizure interval or seizure severity. In one embodiment, a seizure severity index may be defined as one-third of the sum of the standardized natural log of intensity of the seizure, the standardized natural log of duration of the seizure, and the standardized natural log of extent of spread of the seizure. Other seizure severity measures may be used.

A plurality of independent variables may also be selected at 210.

If a determination is made at 220 that the dependent variables may not have been obtained for a desired number of seizures, (e.g., the number of seizures for which values of the dependent variables has been acquired may be too low to be clinically or statistically significant), flow returns to select a plurality of variables at 210.

After 220, if the dependent variable has been selected for a desired number of seizures, quantification of at least one relationship between at least one of the plurality of dependent variables and at least one of the plurality of independent variables may be performed at 230. The plurality of independent variables may be selected from whether the seizure was treated with at least one therapy, whether a prior seizure(s) was(were) treated with at least one therapy, a time elapsed since a prior treatment with at least one therapy, a number of seizures since a prior treatment with at least one therapy, a type of therapy, a dose of a therapy (in the case of drugs), a current density (in the case of electrical stimulation), a degree of tissue cooling or warming (in the case of thermal energy), a time of day the seizure occurred, a time of month the seizure occurred, a time of year the seizure occurred, a level of consciousness (e.g., awake or asleep), a level and type of cognitive activity, a level an type of physical activity, a state of health, the concentration of medicaments or chemicals in a tissue, or two or more thereof. The at least one relationship may be selected from an immediate result of a treatment with at least one therapy, a "carry-over" effect of a treatment with at least one therapy, or two or more thereof. The quantification at 230 may comprise regression analysis on the dependent variables and the independent variables.

If at least one therapy is performed, such as an electrical stimulation of the brain, an electrical stimulation of a cranial nerve, a drug, a thermal treatment of a neural structure, or two or more thereof, an efficacy of the therapy may be assessed at 240.

It should be borne in mind that therapy need not be performed and is optional. Thus, an assessment at 240 need not be performed in every embodiment in accordance with the present disclosure.

After an assessment of efficacy of the therapy, if any, at 240, flow then returns to the acquisition at 210.

Figure 3:
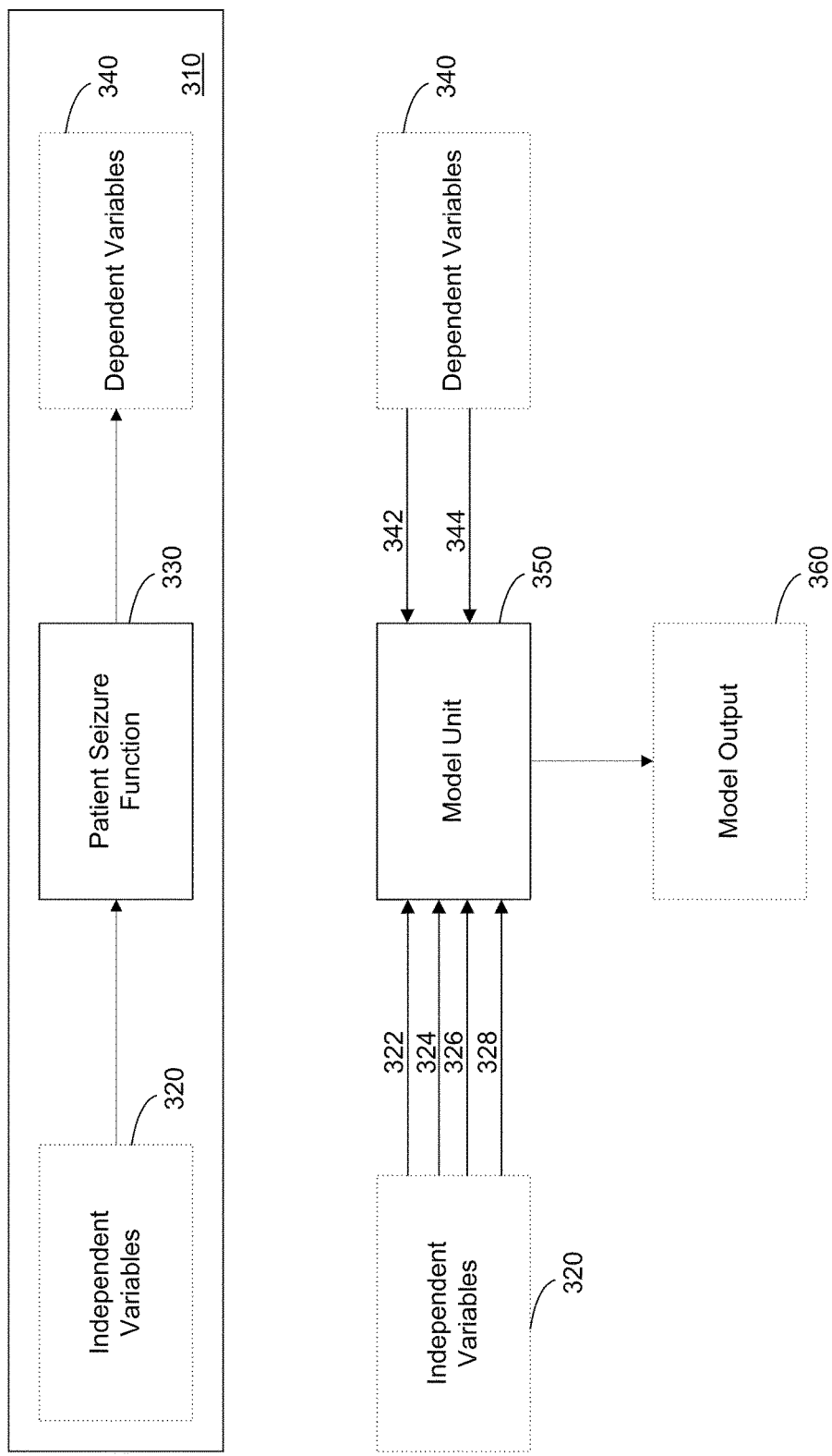
FIG. 3 provides a block diagram of a model unit, its inputs, and its outputs, in accordance with one illustrative embodiment of the present disclosure.
Figure 4A:
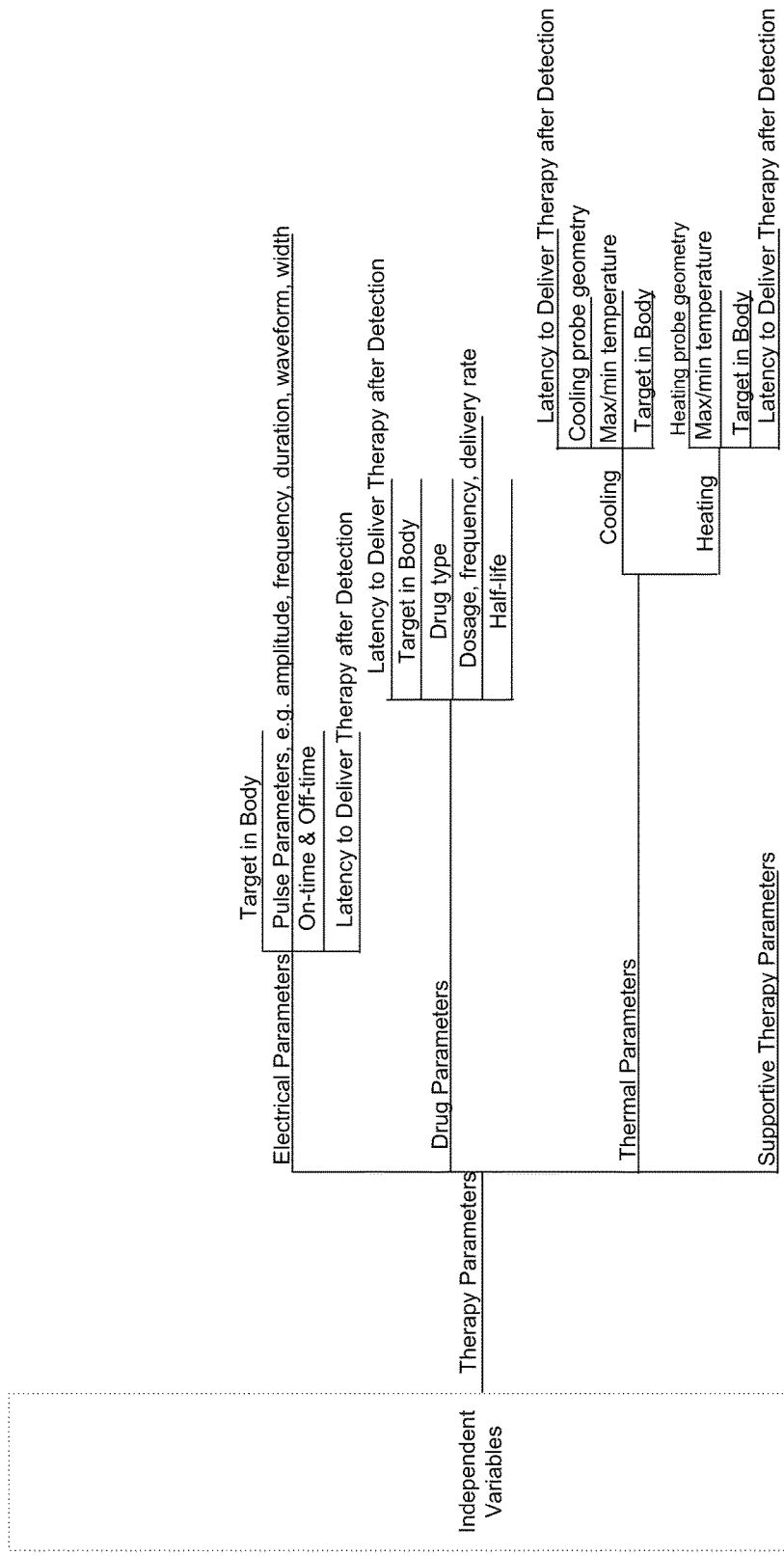
FIG. 4 provides a tabular depiction of a number of exemplary independent variables, in accordance with one illustrative embodiment of the present disclosure.
Figure 4B:
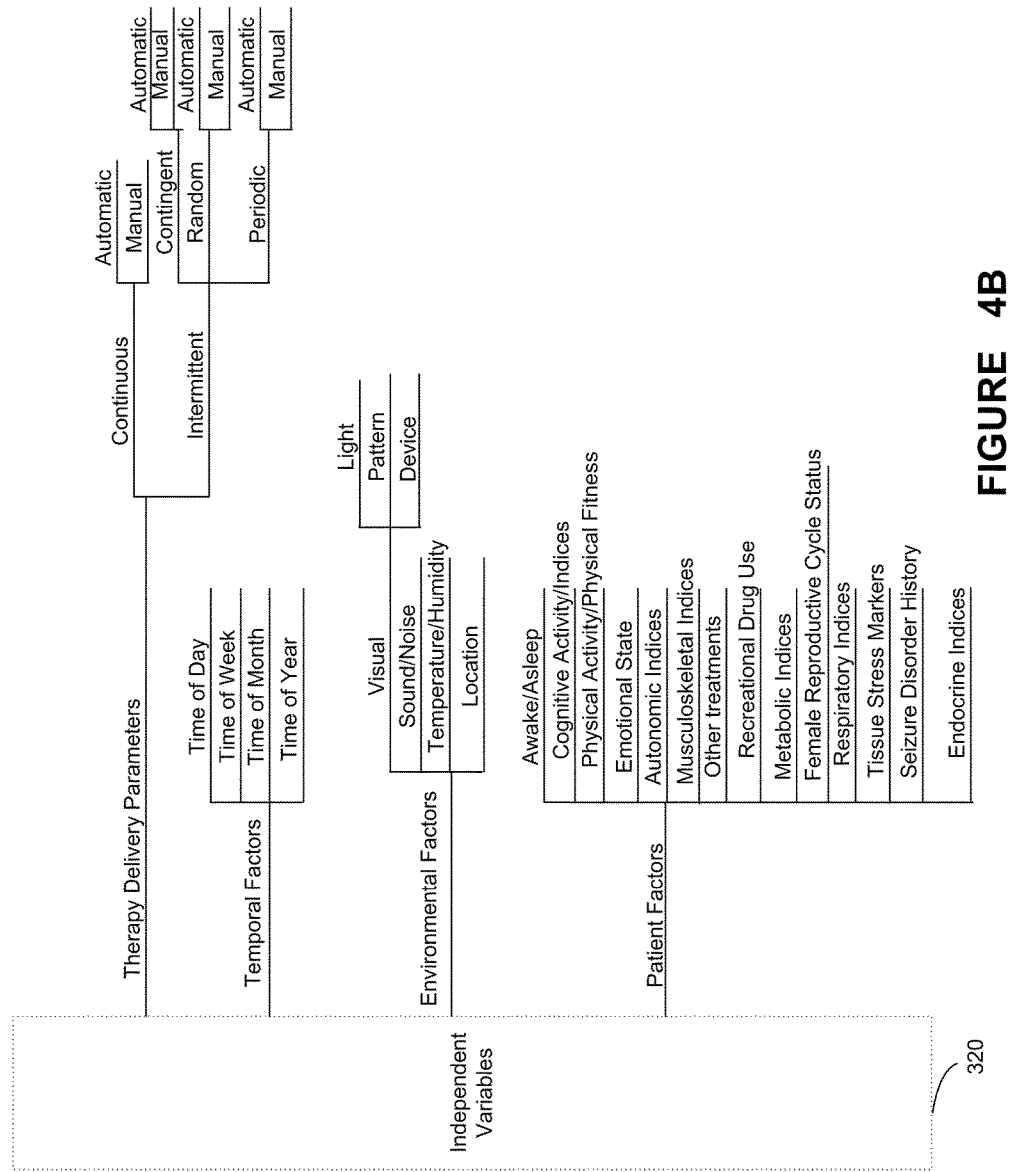

Turning to FIG. 3, in a patient's brain 310, one or more independent variable(s) 320 may be considered as inputs to a patient seizure function 330. In one embodiment of this disclosure, the patient seizure function 330 may be considered a "black box." Therefore, in one embodiment, characterization or analysis of the output of the black box may be useful in determining the activity of the black box and using this in turn to affect therapy. The patient seizure function 330 may be considered to generate outputs relating to the patient's seizures as dependent variables 340. Specific classes of independent variables 320 include, but are not limited to, therapy parameters 322, temporal factors 324, environmental factors 326, and patient factors 328, among others. FIG. 4 lists exemplary independent variables 320 in more detail. In embodiments wherein a plurality of independent variables 320 may be selected, each independent variable 320 may be independently selected from any branch and any level of the branching depicted in FIG. 4. In some embodiments, therapy parameters defining one or more types of therapy may be included as independent variables. In some embodiments, environmental factors, patient factors, and/or temporal parameters may be included as independent variables to assess their effect upon seizure dependent variables.

Specific classes of dependent variables 340 include, but are not limited to, seizure effect data 342 or patient effect data 344 (e.g., adverse effects, safety, tolerability).

Independent variables 320 and dependent variables 340 may be inputs to a model unit 350. The model unit 350 may be capable of performing one or more analyses to quantify and classify (e.g., positive effect) a relationship between at least one independent variable(s) 320 and at least one dependent variable(s) 340. The model unit 350 may be capable of performing a regression analysis. In statistics, regression analysis includes any techniques for modeling and analyzing several variables, when the focus is on the relationship between a dependent variable (e.g., therapeutic efficacy or adverse effects) and one of a plurality of independent variables (e.g., the effect of varying the frequency of electrical stimulation on at least one of seizure frequency, intensity, etc.). Regression analysis provides information of how a dependent variable changes as a function of changes in one of the independent variables, while keeping other independent variables constant. Less commonly, the focus is on a quantile, or other location parameter of the conditional distribution of the dependent variable given the independent variables. In regression analysis, it is also of interest to characterize the variation of the dependent variable around the regression function, which can be described by a probability distribution.

Alternatively or in addition, the model unit 350 may be capable of performing other methods of analysis. Other methods that may be used include, but are not limited to, Bayesian methods (e.g. Bayesian linear regression), least absolute deviations/quantile regression, nonparametric regression, distance metric learning, Pearson product-moment correlation coefficient, or fraction variance unexplained, among others.

Whatever analysis method may be used, the model unit 350 generates a model output 360. The model output 360 may comprise a vector (e.g., a magnitude and direction), a vector field, a scalar, or two or more thereof.

Figure 5:
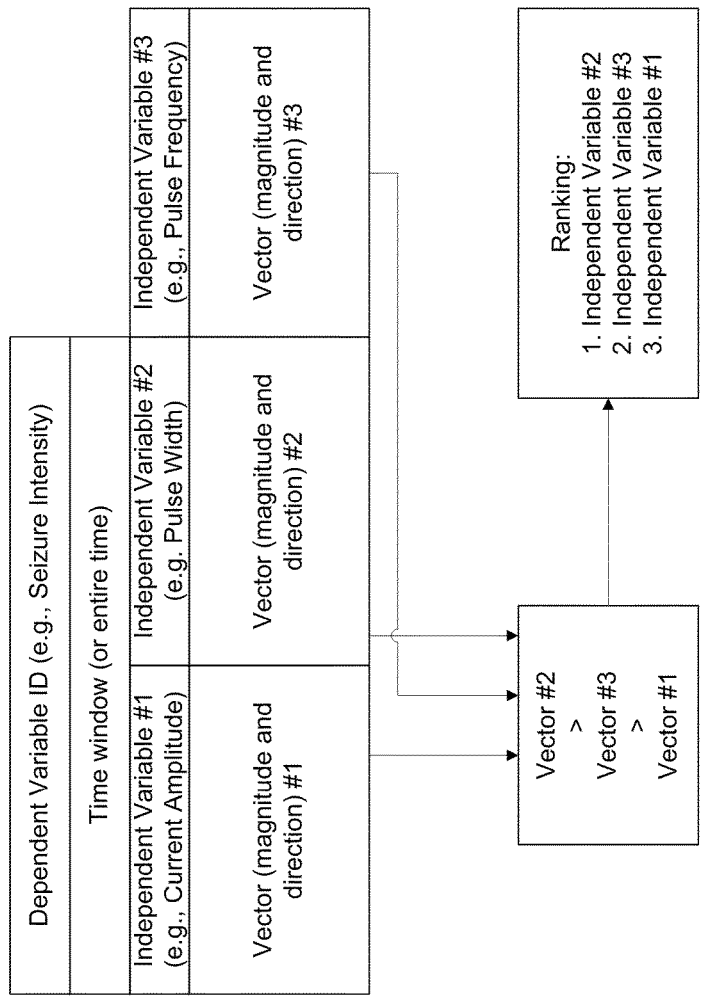
FIG. 5 depicts exemplary outputs of a model unit, in accordance with one illustrative embodiment of the present disclosure.

Exemplary model outputs 360 are shown in FIG. 5 and FIG. 6.

FIG. 5 depicts a table reflecting hypothetical, exemplary relationships (shown as vectors having magnitudes and directions) between each of three independent variables (electrical stimulation therapy current amplitude, electrical stimulation therapy pulse width, and electrical stimulation therapy pulse frequency) on a dependent variable (seizure intensity). The relationship may hold for seizures occurring during an entire time period for which data is available, or it may relate to only seizures occurring during a time window within the entire time period. The relationships in FIG. 5 are illustrative only, and are not intended to reflect relationship embodied in actual patient data.

The three vectors may be used to rank the three independent variables by the magnitude and direction of the vectors. In the hypothetical example shown in FIG. 5, vector #2, representing a relationship between pulse width and seizure intensity, is greater than vector #3, representing a relationship between pulse frequency and seizure intensity, which in turn is greater than vector #1, representing a relationship between current amplitude and seizure intensity. From these comparisons between the vectors, the three independent variables (in this example, pulse width, pulse frequency, and current amplitude) may be ranked based on their magnitude and "direction" (e.g., positive/beneficial, negative/detrimental). The vectors and the rankings may be considered indicators of which independent variables have the strongest relationship with the dependent variable, i.e., which independent variables have the greatest impact on the dependent variable. From this, a physician may conclude the highest ranked independent variables are the ones that may most fruitfully be adjusted to enhance desirable effects on the dependent variable (e.g., in the hypothetical example of FIG. 5, a doubling in pulse width may yield a greater reduction in seizure intensity than would be expected for a doubling in pulse frequency). The therapeutic value of an independent variable is not solely determined by its ranking but also by its effect (e.g., positive or negative) on a dependent variable. For example, in the face of only two possible choices (a highly ranked independent variable with a negative effect vs. a low ranking variable with a beneficial effect), selecting the weakly positive one may be desirable. Alternatively or in addition, if an independent variable over which the physician has no control (e.g., time of day) is ranked highly, the physician may conclude that therapy may have less or more impact during this time period than otherwise and take into account when assessing efficacy.

Quantifying one or more relationships, and/or the magnitude and direction of a relationship between independent and dependent variable, and/or ranking them, may allow a narrowing of the search space during optimization of a therapy, thus expediting the "identification" of a beneficial therapy. Another benefit may be finding optimal ranges of a particular therapy parameter under certain circumstances (e.g. at a particular time of day), which may allow extending battery life (by keeping an electrical stimulation therapy parameter below a point of diminishing or detrimental returns) and/or improving efficacy (by keeping an electrical stimulation therapy parameter above a point where the stimulation may have too low an energy to be efficacious).

FIG. 6 depicts a table reflecting other hypothetical, exemplary relationships (shown as vectors having magnitudes and directions (positive or negative) between one independent variable (e.g., current amplitude in this example) and a plurality of dependent variables (seizure intensity, seizure duration, extent of seizure spread, inter-seizure interval, and seizure severity) over two different time scales discussed elsewhere herein, an immediate time frame and a carryover time frame. The magnitudes shown here are normalized and are relative to a baseline case without electrical stimulation. In other embodiments, normalization may not be performed. Generally, for electrical stimulation therapy, the independent variables would not be expected to have any immediate effect upon ISI, except for the rare situation where stimulation duration exceeds the duration of the seizure. FIG. 6 also depicts a situation wherein an independent variable may have an immediate detrimental effect on one or more seizure variables), but has a beneficial "carry over" effect on one or more future seizures.

The relationships in FIG. 6 are illustrative only, and are not intended to reflect relationship embodied in actual patient data.

Figure 7:
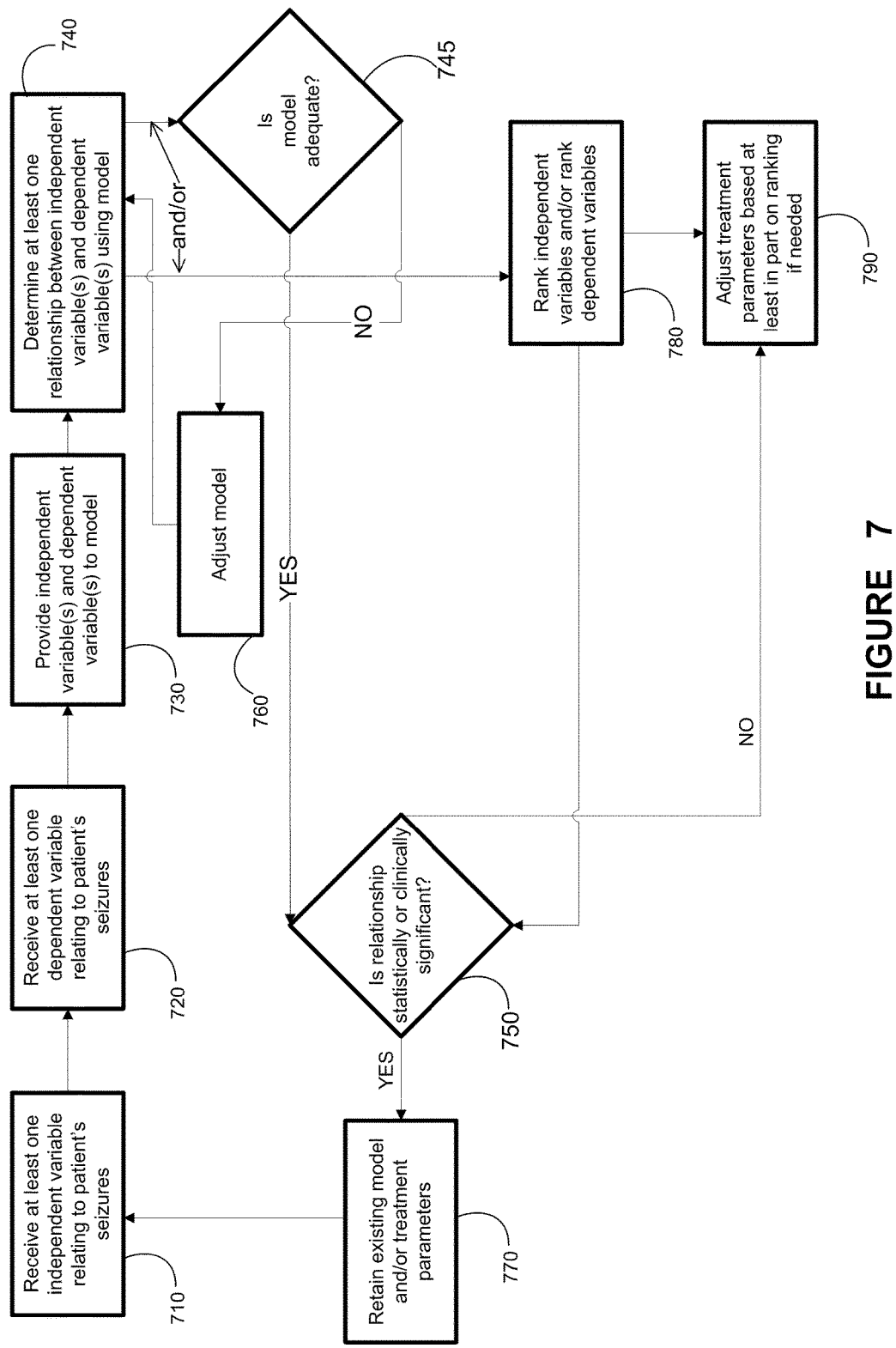
FIG. 7 shows a flowchart of an implementation of a method, in accordance with one illustrative embodiment of the present disclosure.

Turning now to FIG. 7, a flowchart is presented depicting a performance of a method according to one illustrative embodiment of the present claims. At least one independent variable relating to the patient's seizures may be received at 710. "Received" encompasses reception of stored data in a memory, a local database, a remote database, etc.; a determination from sensed data, or a derivation/transformation from sensed data.

Similarly, at least one dependent variable relating to the patient's seizures may be received at 720. The reception of the dependent variable(s) may involve the same or a different technique as the reception of the independent variable(s).

However received, the independent variable(s) and dependent variable(s) may be provided to a model at 730. The model may be capable of performing one or more of the analyses discussed in reference to the model unit 350 depicted in FIG. 3, above.

The model may then be used to determine at least one relationship between the independent variable(s) and the dependent variable(s) at 740. The relationship(s) may be represented by a vector, a vector field, a scalar, or two or more thereof.

Figure 8:
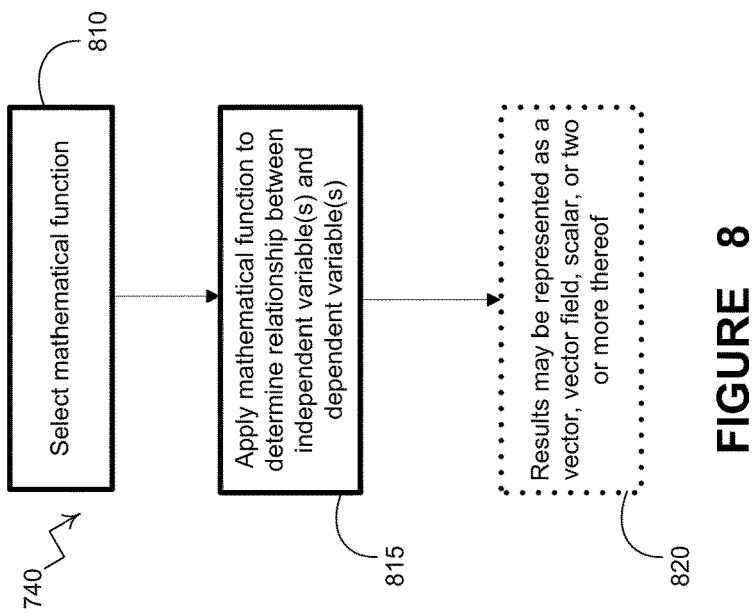
FIG. 8 shows an element of the flowchart of FIG. 7 in more detail, in accordance with one illustrative embodiment of the present disclosure.

FIG. 8 shows the determining at 740 in more detail. A mathematical function may be selected at 810 and applies at 815 to determine the relationship between independent variable(s) and dependent variable(s). The results at 820 may comprise a vector (e.g., a magnitude and a direction), a vector field, a scalar, or two or more thereof.

Though not shown, the results at 820 may be considered in characterizing the relationship in qualitative terms, i.e., a vector having a value greater than about +0.4 may be qualified as a "significant positive" relationship.

Returning to FIG. 7, after 740, flow may follow either or both of two different routes. In one route, a decision is made at 745 whether the model is adequate. This decision may be made based on whether the goodness of fit of the model has a value that meets or exceeds a predetermined standard of adequacy. If the model is found inadequate, in some embodiments, the model may be adjusted at 760. Adjustment of the model may comprise adding or removing one or more independent variable(s), adding or removing one or more dependent variable(s), selecting one or more alternative and/or additional analysis methods, changing the mathematical function describing the relationship between the independent variable(s) and the dependent variable(s), or two or more thereof, among others. After adjustment at 760, flow may return to the determination of the at least one relationship at 740.

If the model is found adequate at 745, flow passes to a decision to be made at 750 as to whether the relationship is statistically or clinically significant. If it is, the existing model and/or treatment parameters may be retained at 770, from where flow may loop back to 710. If the relationship is found to not be statistically or clinically significant, treatment parameters may optionally be adjusted at 790 (discussed in more detail below).

In one embodiment, a "bottom up"/incremental approach to regression analysis may be followed, wherein the first analysis may be between one or a few independent variable(s) and one or a few dependent variable(s). The strength of their relationship may be assessed (using for example a scatter plot) and, if weak/unsatisfactory, the number of independent variables may be increased as needed to improve the fit. In some instances, the fit may not improve despite increasing the number of independent variables as a cause of the poor fit. In such instances, provided the "omitted variable bias" has been excluded, the possibility that the relationship between independent and dependent variables may be a) non-linear or b) unstable (the problem of "random" or "time varying" coefficients) may then be addressed.

In an alternative embodiment (not shown in FIG. 7), a "top down"/decremental approach to regression analysis may be followed, wherein all/most independent variables may be initially included in the analysis. If the model is adequate to identify satisfactory relationships between the independent and dependent variables, the number of variables may be reduced. If this action degrades the fit, the reduction may be stopped and the model may be endowed with the smallest number of independent variables that preserve "goodness" of the fit. An advantage of this "top down" approach may be a higher probability of rapidly making valid/meaningful interpretation of results than the "bottom up" or incremental approach, but at a higher computational cost.

Returning to FIG. 7, a ranking may be performed at 780. The ranking may comprise a ranking of independent variables and/or a ranking of dependent variables based on the magnitude, direction, and/or and classification as positive/beneficial, negative/detrimental, or substantially neutral. The latter ranking and classification may yield information suitable for determining which dependent variables are most susceptible to change upon changes in independent variables. This information may guide the ranking of independent variables to be performed for one or a few dependent variables, but need not.

In other embodiments, all effects in a set or subset of seizure data may be ranked based on a single dependent variable. The rankings may be normalized to a standard scale, e.g., 0-1 in some embodiments, while in other embodiments more useful information may be obtained without normalizing the rankings Normalized rankings may be helpful in analysis of seizures for which a non-normalized output would lack clinical significance. For example, a convulsion typically has higher dependent variable rankings than a complex partial seizure. If attention is only paid to a hypothetical, exemplary, and illustrative only observation that both the convulsion and complex partial seizure saw decreases (benefits) in seizure duration by 0.5, the following difference in clinical impact would be overlooked. Even if its duration decreased from 10 minutes to 5 minutes, a convulsion of the latter duration would remain a convulsion. On the other hand, a reduction in the duration of a complex partial seizure from 1 min to 0.5 min may be sufficient for what would have been a complex partial seizure to instead only manifest as a simple partial seizure. The simple partial seizure would be expected to preserve the patient's awareness (a beneficial effect), which a complex partial would not.

Figure 9:
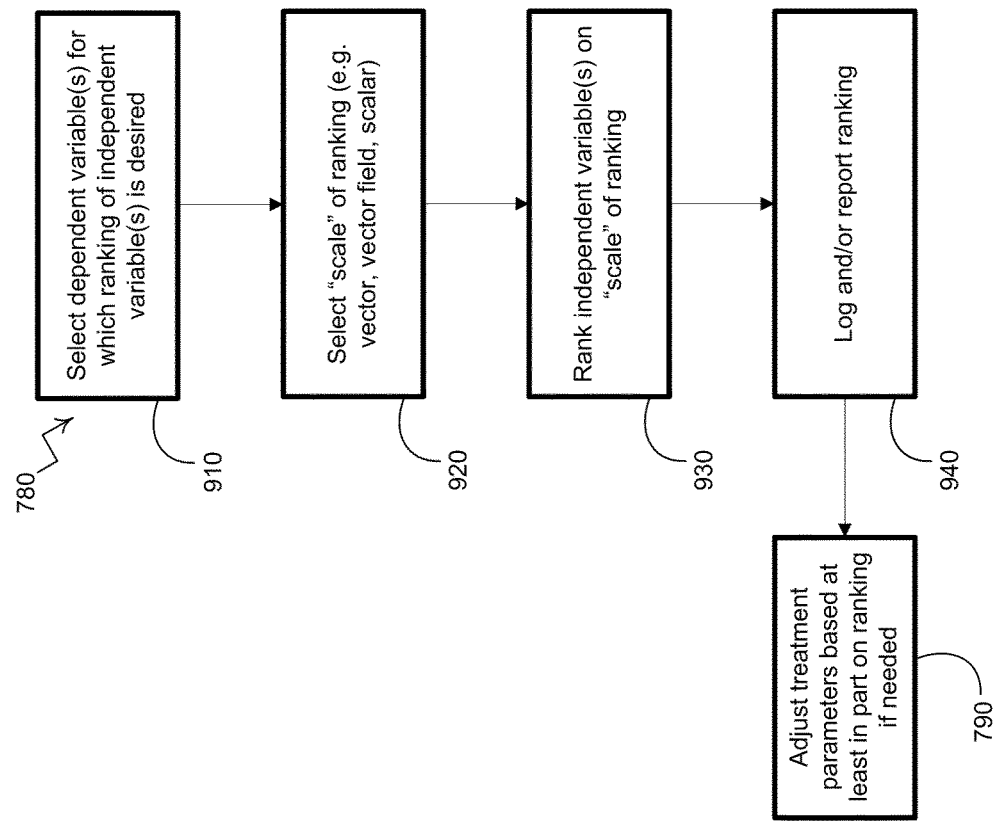
FIG. 9 shows another element of the flowchart of FIG. 7 in more detail, in accordance with one illustrative embodiment of the present disclosure.

FIG. 9 shows one embodiment of the ranking at 780 in more detail. In the depicted embodiment, at least one dependent variable(s) may be selected at 910 for which ranking of independent variables is desired. The at least one dependent variable(s) may be selected based on the magnitude and direction, and/or it may be selected based on other reasons.

A "scale" for ranking (e.g., a vector, a vector field, or a scalar, and which specific one if multiple vectors, etc. are available) may be selected or otherwise provided at 920. The independent variable(s) may be ranked/classified according to the ranking scale at 930. The ranking may be stored and/or reported at 940.

Returning to FIG. 7, after ranking is performed at 780 and/or after a relationship is found to be not significant at 750, flow may then pass to an optional adjustment of treatment parameters at 790. This optional adjustment of one or more characteristics of treatment parameters may be based at least in part on the ranking at 780.

In one embodiment, a method according to the present disclosure comprises selecting a plurality of dependent variables relating to each of a plurality of seizures in a patient; selecting a plurality of independent variables, wherein each independent variable comprises a therapy parameter, a therapy delivery parameter, a temporal factor, an environmental factor, or a patient factor; quantifying at least one relationship between each of at least two dependent variables and each of at least two independent variables; and performing an action in response to said quantifying, selected from reporting said at least one relationship, assessing an efficacy of a therapy, assessing an adverse effect of said therapy, providing a therapy modification recommendation, or adjusting said therapy.

As an illustrative example, quantifications of relationships may be made between a first independent variable (IV-1) and a first dependent variable (DV-1), as well as between IV-1 and a second dependent variable (DV-2). Similarly, quantifications of relationships may be made between a second independent variable (IV-2) and DV-1, as well as between IV-2 and DV-2. Similarly, the quantifications of relationships may be made between DV-1 and IV-1, as well as DV-1 and IV-2. Similarly, quantifications of relationships may be made between DV-2 and IV-1, as well as between DV-2 and IV-1.

Figure 10:
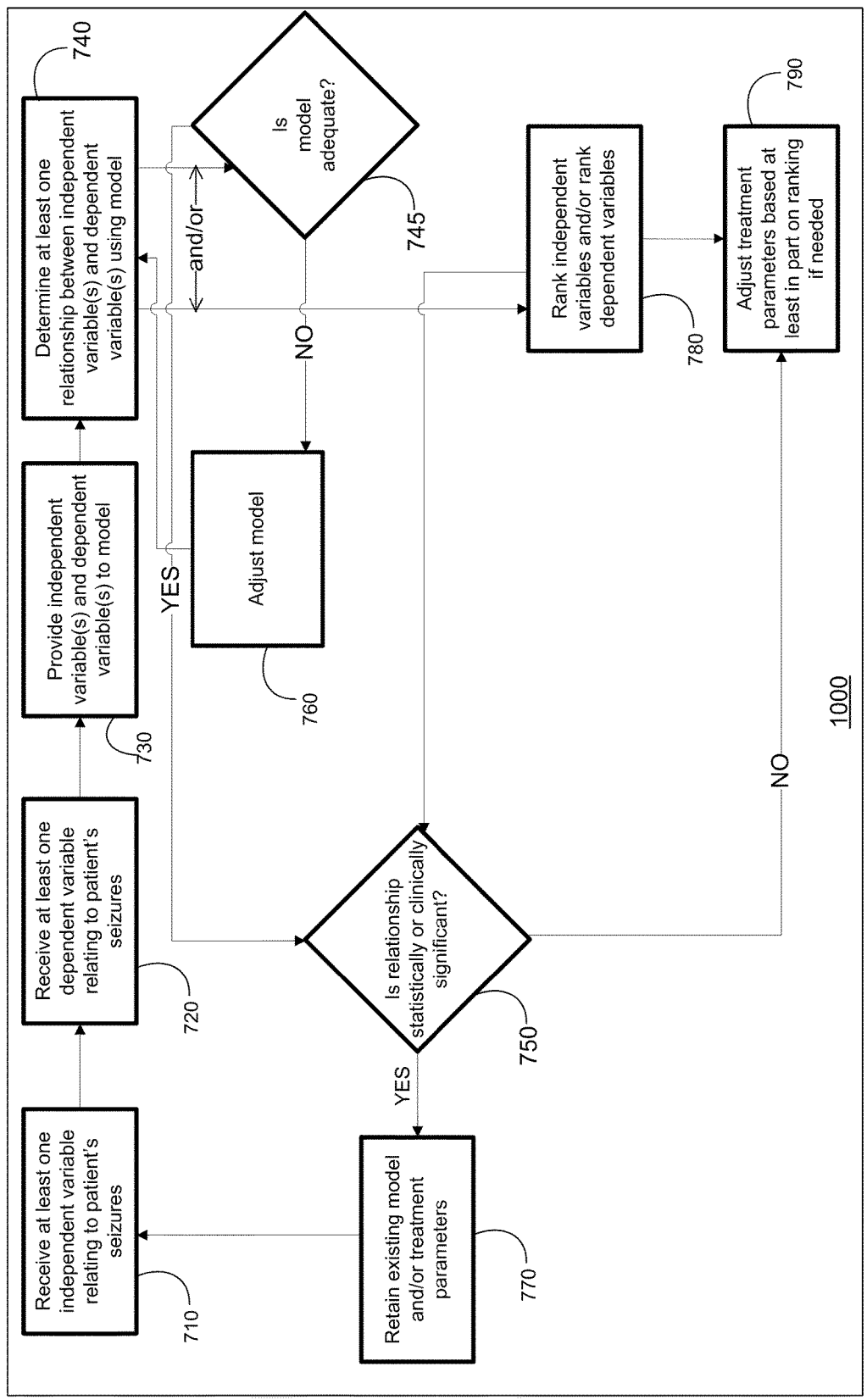
FIG. 10 provides a block diagram of a computer executing instructions contained in a non-transitory computer readable program storage medium that perform an implementation of a method, in accordance with one illustrative embodiment of the present disclosure.

In one embodiment, the method shown in FIG. 2 or 7 may be performed by a computer executing instructions contained in a non-transitory computer readable program storage medium. The computer may be a desktop, laptop, PDA, cellphone, tablet computer, or the like. For example, FIG. 10 depicts a computer 1000 performing the method shown in FIG. 7.

Methods may be implemented in a variety of ways including, but not limited to, machine readable storage devices, various processor-based and computer devices, mechanical devices and/or in networks/systems, and the like. Devices may be internal to a patient or external, and assessing efficacy may likewise be conducted internally in a device, or externally in a separate device that is either communicatively coupled to an internal device or a stand-alone device. Ways of assessing a therapeutic efficacy of seizure treatment may be done using any or all of those described herein in addition to similar methods that would become apparent to those of skill in the art having the benefit of this disclosure. The terms "assessing," "treating," "determining," and/or any other terms used in claims, may be done by direct and/or indirect approaches.

In one embodiment, the present disclosure discloses a method that may comprise treating a seizure using at least one of contingent, periodic or randomly-timed delivery of electrical stimulation; determining at least one parameter (e.g., an independent variable) associated with the seizure; and assessing a therapeutic efficacy of seizure treatment using the at least one parameter.

In one embodiment, the present disclosure discloses an apparatus that may comprise a module adapted to treat a seizure using at least one of contingent, periodic or randomly-time electrical stimulation; a module adapted to determine at least one parameter associated with the seizure; and a module adapted to assess a therapeutic efficacy of seizure treatment using the at least one parameter.

In one embodiment, the present disclosure discloses a non-transitive, computer program storage device containing instructions for performing the method that may comprise treating a seizure using at least one of contingent, periodic or randomly-timed electrical stimulation; determining at least one parameter associated with the seizure; and assessing a therapeutic efficacy of seizure treatment using the at least one parameter.

In one embodiment, the present disclosure discloses a processor-based computing device that may comprise a processor; and a module coupled to the processor, the module adapted to: treat a seizure using at least one of contingent, periodic or randomly-timed electrical stimulation; determine at least one parameter associated with the seizure; and assess a therapeutic efficacy of seizure treatment using the at least one parameter.

In one embodiment, the present disclosure discloses a system, comprising a first module adapted to treat a seizure using at least one of contingent, periodic or randomly-timed electrical stimulation; a second module coupled to the first module, the second module adapted to determine at least one parameter associated with the seizure; and a third module coupled to at least one of the first module or the second module, the third module adapted to assess a therapeutic efficacy of seizure treatment using the at least one parameter.

In one embodiment, the present disclosure discloses an implantable medical device comprising at least one of a seizure treatment unit capable of using at least one of contingent, periodic or randomly-timed electrical stimulation, a determination unit capable of determining at least one parameter associated with the seizure, or an assessment unit capable of assessing a therapeutic efficacy of seizure treatment using the at least one parameter.

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

EXAMPLE 1

Towards a Quantitative Multivariate Analysis of the Efficacy of Anti-Seizure Therapies (The text, tables, and figures of Example 1 have been published by I. Osorio, et al., Epilepsy & Behavior 18 (2010) 335-343, available online on Jun. 11, 2010).

Abstract

Seizure frequency is the only variable used for assessing therapeutic efficacy. Advances in quantitative analyses allow measurement of intensity, duration, spread and time between seizures (TBS). These variables are used here to investigate the efficacy of brain electrical stimulation in humans with pharmaco-resistant seizures.

The results of a trial of contingent high frequency electrical stimulation (HFES) for abatement of clinical and subclinical seizures are examined using Principal Component analysis (PCA) and regression models.

HFES significantly: a) Decreased seizure severity in ⅖ and increased TBS in ⅛ subjects; b) Decreased seizure severity in the primary epileptogenic zone of one subject but increased it in the secondary zones; c) Had a beneficial effect on severity (reduction) and TBS (increase) in the remainder. These effects were immediate and also outlasted the duration of stimulation ("carry-over").

Contingent HFES has multifarious and complex effects, intra- and inter-individually, on seizure severity and TBS. Two inferences, at once promising and sobering may be drawn from these results: one, that contingent electrical stimulation deserves a place in the armamentarium of therapies for pharmaco-resistant seizures, and the other that its apparently narrow therapeutic ratio calls for careful implementation and multivariate quantification of its effects.

Introduction

The assessment of efficacy of anti-seizure treatments and indirectly the foundations of clinical epileptology rest on seizure diaries, which are not only grossly inaccurate [1,2] but also fail to quantify relevant variables such as intensity, duration and extent of spread that provide a measure of seizure severity and would allow assessment of their evolution over long time scales.

Technological advances [3-6] currently allow quantification of intensity, duration, extent of spread (number of electrode contacts registering seizure activity), and of the time between seizures (TBS). The observation that successive seizure occurrence and severity may be correlated [7,8] and that seizure intensity, duration, spread and TBS appear to respond differentially to electrical currents (as will be shown below), underscore the importance of quantifying these variables and of multivariate analysis of the effects of anti-seizure therapies.

Brain electrical stimulation (BES) for treatment of pharmaco-resistant epilepsy is the subject of intense research interest. An in-patient trial of contingent high frequency (>100 Hz) BES in subjects with pharmaco-resistant epilepsy showed marked reduction in clinical seizures [6]. Although the afore-referenced trial is quite small, its depth of analysis and attention to relevant details (all automated detections and stimulations were visually reviewed by an independent expert) cannot be matched by larger trials since they rely mainly [9] or solely [10] on seizure diaries for assessment of efficacy.

Epileptic seizures are subject to multiple sources of variation (i.e., circadian, sleep-wake cycle, hormonal, drug serum concentrations, etc.), and as a consequence appropriate statistical tools are required for their objective characterization.

Through the application of principal component analysis [11] and linear regression models [4, 12] to the in-patient trial data [6], this study derives quantitative seizure descriptors that take into account not only the effects of therapy but also potentially confounding factors such as their intrinsic variability in frequency, circadian cycle influences [4, 13] and the presence of serial correlation [7, 8] among seizures. The measures thus derived have useful clinical applications and provide valuable insight into the complex and multifarious effects of high frequency electrical stimulation on seizures.

Methods and Materials

This in-patient trial was conducted at the University of Kansas Medical Center, with approval from the Human Subjects Committee and the FDA (IDE G9990238) on eight subjects with pharmaco-resistant epilepsies undergoing invasive evaluation for possible surgery [6]. Subjects were enrolled in the order of admission.

The trial consisted of a control phase which corresponded to an invasive surgical evaluation, followed by an experimental phase during which automated seizure blockage using electrical stimulation was attempted. The durations of the phases varied for each individual. Anti-seizure drugs were either discontinued or their dosage decreased at admission; their reintroduction, increases in dosage, or the use of rescue medications at any time during the experimental phase would have led to termination of the subject's participation in the trial and exclusion of the data from analysis.

Electrodes were placed intracranially in all subjects before the control phase. Each subject served as her/his own control and was assigned to one of two groups: 1. The Local Closed-Loop, or 2. Remote Closed-Loop. In 4 subjects assigned to the "local" group, seizures originated from a single discrete area and were thus good surgical candidates. In these subjects, high frequency electrical stimulation was delivered at or near the epileptogenic zone, and the electrocorticogram (ECoG) was acquired through contacts adjacent to those used for stimulation. In 4 subjects included in the "remote" group, seizures originated independently from two or more sites. In these inoperable subjects, electrodes (Medtronic DBS 3387-40; Medtronic, Minneapolis, Minn.) were implanted stereotaxically into each anterior thalamic nucleus after completion of the control phase for delivery of high frequency electrical pulses. These subjects were allowed to recover from general anesthesia for 24 hours before initiation of the experimental phase. ECoG was recorded through the electrodes used for localization of the epileptogenic zones.

ECoG was analyzed with a previously validated algorithm [3, 5] that quantifies seizure intensity, duration, and extent of spread; this algorithm's output was the basis for delivery of electrical stimulation to every other detected seizure. For this study, seizures were defined as any automated detection reaching an intensity threshold, $T=22$, for a minimum duration, $D=0.84$ seconds [3, 5] with or without clinical manifestations. All detections were verified a posteriori through visual analysis performed by an independent expert reviewer. Seizures were classified as either clinical (visible manifestations or event button activation) or electrographic (no visible manifestations or event button activation). The procedures for capturing and verifying automated detections (true positive vs. false positive) or event button presses, and for grouping multiple seizure detections into a single detection cluster if separated by less than 60 s, were described in detail in a previous publication [5].

Hardware, Software, Stimulation Parameters, and Procedures to Assess Safety and Tolerability A system for real-time seizure detection and contingent delivery of electrical currents (Flint Hills Scientific, Lawrence, Kans.) [14] was placed at the bedside and connected through optical isolation to commercial video-EEG equipment (BMSI, Nicolet) and to a constant current stimulator (S-12; Grass Instruments, West Warwick, R.I.) for controlled delivery of biphasic, charge-balanced square pulses. High frequency electrical stimulation (HFES) was defined as 100 Hz minimum (for rationale see [6]), and charge density (pulse width was 100 or 200 usec/phase) for each set of parameters remained below the accepted safety limit of 30 uC/cm$^2$/phase [15]. HFES duration was 1 s. for the local closed-loop group and 30 s. for the remote closed-loop group, with the option of redelivery limited, for safety, to a maximum of five re-stimulations per detection.

For the "local" group, mean stimulation frequency was 251.5 Hz (range: 50-500 Hz), mean intensity was 5 mA, and mean duration was 1 s. For the "remote" group, mean stimulation frequency was 151.5 Hz (range: 100-200 Hz), mean intensity was 5.4 mA (range: 1.5-8.5 mA), and mean duration was 21.75 seconds (range: 2.5-30 seconds). Table 1 and reference [6] contains detailed information about all the stimulation parameter configurations used in this trial.

TABLE 1

| Subject | Config. No. | Frequency (Hz) | Intensity (mA) | Duration (s) | PW (μs/Phase) | Location code | No. of Clusters |
|---|---|---|---|---|---|---|---|
| LCL-1 | 1 | No stimulation | | | | | 344 |
| | 4 | 50 | 10 | 1 | 200 | 2 | 5 |
| | 5 | 333 | 10 | 1 | 200 | 1 | 4 |
| | 6 | 333 | 10 | 1 | 200 | 2 | 10 |
| | 7 | 500 | 10 | 1 | 200 | 2 | 7 |
| LCL-2 | 1 | No stimulation | | | | | 81 |
| | 6 | 125 | 5 | 1 | 100 | 3 | 4 |
| LCL-3 | 1 | No stimulation | | | | | 666 |
| | 2 | 100 | 5 | 1 | 200 | 1 | 3 |
| | 3 | 125 | 5 | 1 | 200 | 1 | 11 |
| | 4 | 225 | 5 | 1 | 200 | 1 | 4 |
| LCL-4 | 1 | No stimulation | | | | | 83 |
| | 7 | 100 | 5 | 1 | 100 | 3 | 2 |
| RCL-1 | 1 | No stimulation | | | | | 169 |
| | 13 | 100 | 1.5 | 30 | 100 | 5 | 27 |
| | 18 | 142.9 | 1.5 | 30 | 100 | 5 | 1 |
| | 19 | 142.9 | 2.5 | 30 | 100 | 5 | 2 |
| RCL-2 | 1 | No stimulation | | | | | 2929 |
| | 7 | 100 | 5 | 2.5 | 100 | 3 | 61 |
| | 8 | 142.9 | 5 | 2.5 | 100 | 3 | 92 |
| | 9 | 142.9 | 5 | 30 | 100 | 3 | 118 |
| | 10 | 142.9 | 5.5 | 30 | 100 | 3 | 14 |
| | 11 | 142.9 | 6 | 30 | 100 | 3 | 6 |
| | 12 | 142.9 | 6.5 | 30 | 100 | 3 | 3 |
| | 13 | 142.9 | 7 | 30 | 100 | 3 | 2 |
| | 14 | 142.9 | 8 | 30 | 100 | 3 | 1 |
| | 15 | 142.9 | 8.5 | 30 | 100 | 3 | 46 |
| | 16 | 200 | 5 | 30 | 100 | 3 | 194 |
| RCL-3 | 1 | No stimulation | | | | | 168 |
| | 12 | 100 | 5 | 2.5 | 100 | 6 | 2 |
| RCL-4 | 1 | No stimulation | | | | | 193 |
| | 4 | 100 | 5 | 30 | 100 | 2 | 5 |
| | 5 | 142.9 | 5 | 30 | 100 | 2 | 10 |
| | 7 | 200 | 5 | 30 | 100 | 2 | 10 |

Parameter configurations for electrical stimulation. Each configuration refers to a unique combination of frequency f (Hz), intensity I (mA), duration D (s), pulse width PW (us/phase) and location. Only configurations in which one or more true positive seizure detection clusters were stimulated are reported. Location code refers to specific contacts chosen for stimulation. The number of clusters may differ slightly from that given in Table 2 because certain model parameters (e.g., PStim, SStim) cannot be determined for clusters at the start/end of a stim configuration or near a gap in data collection.

Behavior, vital signs, SaO$_2$, and EKG were monitored before, during, and after at least three manually triggered stimulations, separated by at least 2 minutes, at the initiation of the experimental phase and whenever any of the stimulation parameters was increased. If stimulations elicited adverse effects such as after discharges, intensity was decreased by 0.5 mA until a safe/tolerable level was reached. If intensity, duration, or spread were not reduced by at least 50% after two stimulation trials, the frequency was increased by 50 Hz until any of the following occurred: (1) the desirable effect was obtained; (2) the predetermined frequency limit for the "local" (500 Hz) or the "remote" group (200 Hz) was reached; or (3) there were adverse effects. A parameter configuration set consisted of a pre-specified stimulation frequency, intensity, pulse width, duration, and "geometry", determined by the location of stimulating contacts, their orientation, and their polarity in reference to the epileptogenic zone (Table 1).

Data Processing

Each subject's ECoG was stored on a hard disk together with log files documenting the times of each automated detection, stimulation, and corresponding stimulation parameters. ECoG's were reanalyzed off-line in their entirety to ensure uniformity of algorithm detection parameters between control and experimental phases. A snapshot of ECoG starting 7.5 seconds before and ending 7.5 seconds after the onset of each automated seizure detection was printed and reviewed visually by an independent expert, who classified each detection as either a seizure (true positive), interictal epileptiform discharge(s), or no seizure (false positive). Another 15-second snapshot centered at the time of each stimulation attempt was printed for visual review by an independent expert to ascertain the presence of a stimulation artifact; if no artifact was seen, the attempt was classified as a failed stimulation and the seizure was classified as non-stimulated.

Statistical Analysis

Principal component analysis (PCA) is a standard multivariate method [11] for determining the relative contributions of one or more factors to the overall variability observed in a set of measurements (e.g., seizure intensity, duration, etc.). PCA finds linear combinations such that the first linear combination (principal component 1; PC1) accounts for the largest variation in the original data set, the second linear combination (PC2) accounts for as much of the remaining variation in the data as possible subject to the condition that it is uncorrelated with PC1, the third linear combination (PC3) accounts for as much of the remaining variation in the data as possible while remaining uncorrelated with both PC1 and PC2, and so on. Simply put, PCA identifies the independent/perpendicular directions in which the data varies, and orders these directions by variance from the largest to the smallest. By limiting subsequent analysis to the main principal components responsible for the bulk of data variation and by ignoring the remaining (essentially unused) degrees of freedom in the data, this approach offers an efficient and effective way to control the trade-off between losing information and simplifying analysis of the matter at hand.

Figure 11:
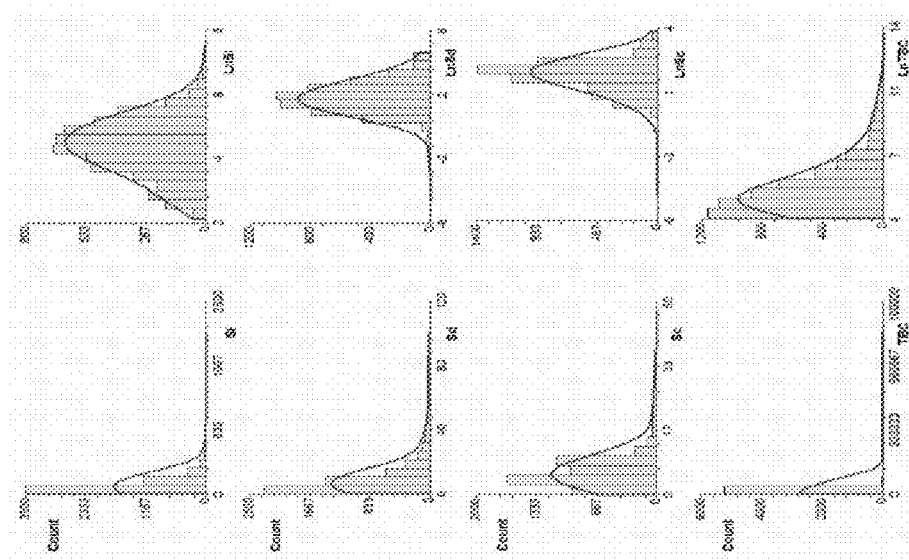
FIG. 11 shows the distributions of values of Seizure Intensity (Si), Seizure Duration (Sd) and Seizure Spread (Sc) (left columns) and the distributions of natural logarithmic (Ln) transformations of the left-column values (right columns), as discussed in more detail in Example 1.

For this study the dependent variables or measurements of interest for each seizure are: 1. Intensity; 2. Duration; 3. Extent of spread (number of electrodes contacts registering seizure activity), and 4. Time (in seconds) elapsed between the end of a seizure and the onset of the next one. A separate principal component analysis (PCA) was carried out on each of the eight subjects (Local Closed-Loop 1-4 and Remote Closed-Loop 1-4). As originally measured, the values of intensity, duration, extent of spread and time between seizures were not normally distributed (FIG. 11) and were thus transformed using natural logarithms (Ln) to "normalize" them and make them more suitable for PCA. The time between seizures for the last recorded seizure in a trial and also during gaps in the recordings (e.g., when subjects were disconnected for imaging studies) is not defined and could not be included in the PCA analysis.

Regression analysis of the principal component measures which represent combinations of intensity, duration, spread and time between seizures, was carried out separately for each subject to quantify the effects, if any, of the following factors or independent variables: (1) Delivery of electrical currents (stimulation) to the seizure under consideration or to previous ones; (2) Time elapsed since the last stimulation; (3) Number of seizures since the last stimulation; and (4) Time of day that a seizure occurred [4, 13].

More specifically, the following factors are considered in the regression models:

1. The time of day (TDay), divided into 6 hour periods: midnight-6 am, 6 am-noon, noon-6 pm and 6 pm-midnight. TDay reflects circadian variation.

2. Study phase (SP): Control phase (CP) which is assigned a value of 0 vs. experimental phase (EP) which is assigned a value of 1.

3. Stimulation (Stim): A value of 0 was assigned to a non-stimulated seizure and a value of 1 to a seizure that was stimulated.

4. Successive stimulations (SStim). In a few instances where the stimulation schedule was incorrectly programmed or unstimulated detections turned out to be false positive, successive seizures were sometimes stimulated instead of every other seizure. If the seizure immediately before the one being presently considered was stimulated, SStim was assigned a value of 1; and if not, the assigned value was 0.

5. Previous stimulations (PStim) are taken into account with this indicator which is 0 if no seizures prior to the one being considered were stimulated, or 1 if any, including the immediately previous seizure, were stimulated. Note that PStim encompasses SStim.

6. Time Post-Stimulation (TPS): Corresponds to the time elapsed since the last stimulation (in hours) and was assigned a value of 0 if no stimulations occurred before the seizure presently considered. The number of seizures since the last stimulation was also considered as a variable, but discarded since it did not provide additional useful information.

By way of example, if the only stimulated seizure SZ(Stim) was that which precedes the one presently under consideration—an example sequence would be SZ(No Stim), SZ(Stim), SZ—then SStim=1, PStim=1 and TPS is the time in hours since the last stimulated seizure. If previous seizures but not the one immediately before the SZ presently under consideration were stimulated—e.g., SZ(Stim), SZ(Stim), SZ(No Stim), SZ—then, SStim=0, PStim=1, and TPS=time in hours since the last stimulated seizure. For a seizure with no previously stimulated seizures, only the time of day and stimulation are included in the regression model since SStim, PStim and TPS are all zero.

7. The Stimulation Parameter Configuration (SPC) used. For example, for subject LCL-1 there were five configurations labeled 1 for no stimulation; 2 for the first stimulation configuration; 3 for the second; 4 for the third; and 5 for the fourth, respectively.

8. Prior Stimulation Parameter Configurations (PSPC) in the case of successive (SStim) or previous stimulations (PStim).

| Model | Terms in the Model |
|---|---|
| A1 | Time of Day (TDay) |
| A2 | TDay + Study Phase (SP) |
| A3 | TDay + SP + Stimulation (Stim) |
| A4 | TDay + SP + Stim + Successive Stimulations (SStim) |
| A5 | TDay + SP + Stim + SStim + Previous Stimulations (PStim) + Poststimulation time (TPS) |
| B3 | TDay + SP + Stimulation Parameter Configuration (SPC) |
| B4 | TDay + SP + SPC + Previous Stimulation Parameter Configurations (PSPC) |
| B5 | TDay + SP + SPC + PSPC + PStim + TPS |

TABLE 2

| Subject | SZ | Stims. | SPC | Variable | % Var | Sig. | Corr. | Terms in Model | Stimulation Effect |
|---|---|---|---|---|---|---|---|---|---|
| LCL-1 | 367 | 25 | 4 | SS | 0.8 | 0.046 | 0.14 | Stim | Beneficial |
| | | | | TBS | 12.1 | <0.001 | None | TDay | None |
| LCL-2 | 84 | 4 | 1 | SS | 25.2 | <0.001 | None | TDay + Stim + SStim1 + TPS | Beneficial & Detrimental |
| | | | | TBS | None | None | None | None | None |
| LCL-3 | 682 | 18 | 3 | SS | 14.5 | <0.001 | 0.29 | TDay + SStim + SPC | Detrimental |
| | | | | TBS | None | None | None | None | None |
| LCL-4 | 81 | 2 | 1 | SS | None | None | None | None | None |
| | | | | TBS | 8.3 | 0.005 | 0.28 | SStim1 | Beneficial |
| RCL-1 | 197 | 33 | 4 | SS | 16.1 | <0.001 | 0.23 | TDay + Stim + SStim + PStim | Beneficial & Detrimental |
| | | | | TBS | 33.1 | <0.001 | 0.76 | TDay + PSPC + PStim + TPS | Beneficial & Detrimental |
| RCL-2 | 3462 | 537 | 10 | SS | 10.1 | <0.001 | 0.32 | TDay + EP + SPC + PSPC + PStim + TPS | Beneficial & Detrimental |
| | | | | TBS | 2.2 | <0.001 | 0.20 | EP + SPC + PStim + TPS | Beneficial & Detrimental |
| RCL-3 | 159 | 2 | 1 | SS | 17.7 | <0.001 | 0.32 | TDay + EP | Not significant |
| | | | | TBS | 19.9 | <0.001 | 0.45 | TDay + EP | Beneficial |
| RCL-4 | 216 | 25 | 3 | SS | 3.7 | 0.003 | 0.30 | Stim | Beneficial |
| | | | | TBS | 11.5 | <0.001 | 0.35 | EP + PSPC | Beneficial & Detrimental |

Table 2. Models and factors considered for estimation of seizure severity and time between seizures (TBS).

Table 2 shows the regression models systematically and incrementally tested for the contribution of potentially relevant independent variables (e.g., time of day, stimulation vs. no stimulation of the seizure under consideration and/or stimulation of the seizure immediately before the one under consideration, etc) to changes (if any) in the value of a dependent variable (e.g., seizure duration). For example, the model: TDay+SP+Stim gives a regression equation for a variable Y as follows:

$$Y = a + b_2\, TDay_2 + b_3\, TDay_3 + b_4\, TDay_4 + c\, SP + d\, Stim,$$

where $a$, $b_2$, $b_3$, $b_4$, $c$ and $d$ are regression coefficients to be estimated, $TDay_i$ is equal to 1 for the period of day being considered (e.g., midnight-6 am) or is otherwise 0, study phase is 0 for the control and 1 for the experimental phase, and Stim is 0 for no stimulation and 1 for stimulation. This approach assesses not only the effect of the therapy, but of other factors that may confound its effects, as will be illustrated particularly with respect to the circadian impact on seizure intensity.

The complexity of the regression models increases from model a1 to a5 through the addition of factors (e.g., Stim), culminating in model a5 that incorporates all factors mentioned above. Models b3 to b5 are similar to models a3-a5, but take into account the different sets of stimulation parameter configurations used and are applicable only to those subjects for which different configurations were tested. Once all of the models a1-a5 and b3-b5 (if applicable) are estimated, either a5 or b5 is selected, depending on which gives the most significant regression equation.

The regression residuals from a fitted model are the differences between the observed values of the dependent variable (e.g., intensity) and the values predicted by the regression equation. Data collected repeatedly over time, such as seizures, is prone to be serially correlated or to show persistence. This means that if the intensity of the present seizure is high, the intensity of the seizure that follows it is likely to high as well. For some subjects the regression residuals display positive serial correlation, which means that there is a tendency for the residuals from successive seizures to be similar. For example, there may be several seizures with observed values considerably higher than expected. If serial correlation in regression residuals [12] is detected in any of the final models considered here, it is taken into account using the option in GenStat [16] to estimate both a regression model and the serial correlation between successive residuals using the principle of maximum likelihood.

To properly interpret the results, the following should be considered: 1. When comparing regression models, the one which accounts for the highest percentage of variability in the data is considered the best; 2. The significance of a regression equation is the probability of getting a fit that is just as good as the equation provides simply by chance, that is, in the absence of a relationship between the dependent variable and those variables to which it is being related. In this sense the most significant regression equations (with the smallest p values) are better than those with larger p values.

Results

The first principal component (PC1) (Table 3) corresponds to a weighted sum of the standardized values of the natural logarithm of seizure intensity, duration and extent of spread and accounts for the majority (52-63%) of the variation in the data. Interestingly, intensity, duration and extent of spread always have approximately the same coefficient values and contribute in similar amounts to PC1. Given this result, these variables may be conflated into one: Seizure Severity. Simply stated and making allowances for lack of statistical rigor, the first principal component encompasses 3 of 4 possible seizure variables/dimensions.

The second principal component (PC2) (Table 3) represents mainly the time between the end of a seizure and the onset of the next one, and accounts for 25% of the variation in the data.

TABLE 3

| | Seizures per Hour | | Change |
|---|---|---|---|
| Subject | CP | EP | % |
| LCL1 | 0.096 | 0.000 | −100.0 |
| LCL2 | 0.037 | 0.015 | −59.5 |
| LCL3 | 0.078 | 0.106 | 36.8 |
| LCL4 | 0.018 | 0.000 | −100.0 |
| RCL1 | 0.075 | 0.021 | −72.8 |
| RCL2 | 0.042 | 0.045 | 5.6 |
| RCL3 | 0.048 | 0.022 | −53.3 |
| RCL4 | 0.049 | 0.025 | −48.6 |
| All | 0.052 | 0.027 | −47.2 |

Table 3. Results of principal components analyses for each of the 8 subjects (LCL 1-4; RCL 1-4, showing for each subject the number of seizure clusters analyzed (Clusters), the coefficients of Ln(Si), Ln(Sd), Ln(Sc) and Ln(ISI) for PC1 to PC4, the variance accounted for by each principal component, the percentage of the total variation that this represents, and the cumulative percentage of variation accounted for by PC1, PC1 & PC2, PC1 to PC3 and PC1 to PC4 (which is always 100%).

PC3 and PC4 account for 12-23% of the data variation and were combinations in different proportions of intensity, duration, spread and the time between seizures. PC3 and PC4 were excluded from further analysis due to their small contribution to the variation in the data.

For simplicity PC1 or its equivalent seizure severity (SS), was replaced in the regression analyses by the average of the standardized values (mean 0, standard deviation 1) of the natural logarithm of intensity, duration and spread so that SS=⅓(Ln Intensity+Ln Duration+Ln Spread), and PC2 was replaced by the natural logarithm of the time between seizures variable. The standardization was done by applying a logarithmic transformation to the values of each then subtracting the mean and dividing by the standard deviation in an effort to transform the raw component data into a distribution approximating standard normal.

Since the first two principal components are effectively measures of seizure severity and recurrence rate respectively, results of regression modeling and the influence of the various factors considered may be interpreted accordingly. Table 4 summarizes the regression results for each subject for whom relevant details are provided below.

Subject LCL-1

The regression analysis was performed on 367 seizures: 290 in the control phase and 77 in the experimental phase (EP). In the EP, a total of 25 seizures were stimulated with 4 different configurations.

Electrical stimulation (Stim, model a3, Table 2) was the only factor with significance at the 5% level, reducing mean seizure severity by 0.359. Allowing for the existence of serial correlations [the Pearson correlation coefficient between one residual and the next is positive (+0.13)] the estimated reduction in severity was 0.393, with the estimated correlation between one regression residual and the next being 0.135, which is significant at the 1% level. No significant differences were observed between the four stimulation configurations used. The time between seizures was not significantly influenced by stimulation or any of the treatment factors considered in the analyses. Time of day effects on time between seizures were positive and significant (p=0.02) for 6 am to noon, noon to 6 pm and 6 pm to midnight, indicating that time between seizures is longer during these periods than from midnight to 6 am.

Subject LCL-2

The regression analysis was performed on 84 seizures: 51 in the control and 33 in the experimental phase (EP). In the EP stimulation was attempted for 25 seizures, but due to failure of a stimulator's battery, only 4 were actually treated, all with the same configuration, making models b3-b5 superfluous.

Stimulation reduced mean seizure severity by 1.854; the effect of stimulations following the first one is estimated to be =−2.373+0.335 (TPS), where TPS is the time elapsed from the previous stimulation. By contrast, for a non-stimulated seizure (during the experimental phase) the effect is estimated to be −0.519+0.335 (TPS). That is, contingent stimulation has the effect of immediately reducing seizure severity, an effect that outlasts the duration of stimulation ("beneficial carry-over" effect). However, the beneficial "carry-over" effect not only decays over time, but at some point "reverses" direction, becoming detrimental. Indeed, the last seizure in the experimental phase, which occurred 11.55 hours after the last stimulation, was the most severe of this phase; the estimated detrimental "carry-over" effect on it was −0.510+0.335×11.55=+3.36, suggestive of a "rebound" effect.

Time of day also impacted severity: Mean seizure severity is significantly higher from noon to 6 pm than from midnight to 6 am, and higher from 6 pm to midnight than from midnight to 6 am, but not significantly higher. The mean severity was similar for midnight to 6 am and 6 am to noon.

None of the factors considered in the regression model had a significant effect on the time between seizures variable.

Subject LCL-3

Six hundred and eighty two seizures were analyzed, 539 in the control and 143 in the experimental phase. Eighteen seizures were stimulated with three different configurations.

The best fitting model for seizure severity (TDay, PStim, and Unique) accounts for 14.5% of the variation in the data. The estimated serial correlation coefficient of 0.294 is very highly significant, providing evidence that the regression residuals are correlated. The model was therefore estimated with an allowance for serial correlation. All three stimulation parameter configurations are estimated to increase mean seizure severity by 0.7-1.7, with highly significant effects for the first two configurations (p≤0.001). Stimulation of the previous seizure increased mean severity of the following seizure by 0.602 for all configurations (p=0.001).

The estimated increases in mean seizure severity corresponded to seizures originating in the secondary epileptogenic zones (frontal lobes), whereas the severity of those of mesial temporal origin (the primary zones), were decreased.

The estimates of the time of day effects indicate that mean seizure severity was lowest (by about 0.30, which is highly significant) from 6 AM to noon and noon to 6 PM than at the other times.

The regression analysis was also carried out on the time between seizures variable but no effects were significant at the 5% level.

Subject LCL-4

Eighty one seizures were suitable for analysis with 62 of these in the control and 19 in the experimental phase (EP). Two seizures were stimulated in the EP with one stimulation configuration.

Electrical stimulation had no effect on severity but significantly reduced the mean of the time between seizure variable, that is, seizure frequency increased. The estimated mean of the natural logarithm of time between seizures before any stimulation was delivered was 8.4 vs. 1.6 after the first stimulation. No other effects were significant.

Subject RCL-1

Analysis was performed on 197 seizures with 61 in the control and 110 in the experimental phase (EP). Thirty three seizures were stimulated in the EP with four different configurations.

Allowing for significant serial correlation stimulation increased the mean severity by 0.432 (p=0.013) and if the previous seizure was also stimulated the intensity of the one presently being treated further increased by 0.469 (p=0.008). However, the severity of a non-stimulated seizure following one that was stimulated was estimated to be reduced by 1.246 (p<0.001). These findings illustrate the presence of an immediate paradoxical (worsening) cumulative effect of stimulation and a of beneficial post-stimulation (carry-over) effect.

Allowing for serial correlation which is very significant (r=0.77, p<0.001) the effect of stimulating the previous seizure using configuration 18 significantly (p=0.019) increased the (log) time between seizures by 3.03. Also the effect of the time since the last stimulation is significant (p=0.033). However, it is estimated that after the first stimulated seizure, regardless of the stimulation configuration (including 18) the mean of the time between seizures drops slightly by 0.087 and then drops by 0.040 for every hour following the last stimulation.

Subject RCL-2

Analysis was carried out on 3462 seizures with 1650 in the control and 1812 in the experimental phase (EP). Electrical currents were delivered to 537 seizures using 10 different stimulation configurations.

The mean severity of all seizures (stimulated and non-stimulated) was lower (by −0.26, p<0.001) in the experimental phase than for seizures in the control phase. There were ten stimulation parameter configurations and their effects on the severity of the seizure under consideration or on the previous seizure are multifarious. Allowing for the presence of serial correlation some effects are significant (p≤0.05): a) Seizure severity is reduced by 0.298 by configuration 15 and by 0.270 by configuration 16; b) Stimulation of the previous seizure with configuration 15 significantly (p=0.008) reduces (by 0.349), the severity of the seizure under consideration; c) Configuration 10 increases seizure severity by 0.571, but stimulation of any seizure before the one under consideration with any configuration reduces severity of present ones by an estimated 0.199 (p=0.010).

The effect of the time elapsed since the previous stimulation on severity is not significant.

All of the fitted models for time between seizures account for a highly significant amount of its variation (p<0.001). However, the model that allows for different stimulation configurations to have different effects was chosen as it fits the data significantly better (p=0.005) than the models that do not allow for differences among configurations. Allowing for highly significant serial correlation (r=0.20, p<0.001), the estimated mean time between seizures is highly significantly (p<0.001) lower (by 0.212) in the experimental than in the control phase. However, stimulation parameter configuration 15 significantly (p<0.001) increased (by 0.446) the mean time between a seizure and the next one. In addition after the first seizure was stimulated with any configuration the mean of the time between seizures was estimated to have increased by 0.073 with a further hourly increase of 0.104. Allowing for the presence of significant serial correlation (r=0.319, p<0.001), seizure severity is significantly (p=0.034) lower from 6 am to midday than from midnight to 6 am, about the same from midday to 6 pm as from midnight to 6 am, and significantly higher from 6 pm to midnight than from midnight to 6 am (p=0.032).

Subject RCL-3

One hundred and fifty nine seizures (92 in the control and 67 in the experimental phase (EP)) were analyzed. Only two seizures were treated in the EP with one stimulation configuration.

All of the fitted models for seizure severity account for a highly significant part of the variation in the data but only the effects of the time of day and the experimental phase are significant at the 5% level. The final model chosen therefore only includes these effects. Since only one stimulation configuration was used, models allowing for different configuration effects are not considered.

Stimulation significantly (p=0.033) increases seizure severity, but if allowance is made for the presence of significant serial correlation (p<0.001) the effect becomes non-significant. With an allowance for serial correlation, seizure severity is highly significant (p<0.001) lower from 6 pm to midnight compared to midnight to 6 am.

The mean time between seizures variable was higher by 1.19 (p=0.004) in the experimental than in the control phase and the estimated time between seizures was significantly higher (p<0.01) for noon to 6 pm and 6 pm to midnight than from midnight to 6 am.

Subject RCL-4

Analysis was performed on 216 seizures with 158 in the control and 58 in the experimental phase (EP). Twenty seizures were treated with three configurations.

Allowing for the highly significant serial correlation (r=0.30, p<0.001), stimulation reduced mean seizure severity by 0.58 (p=0.001).

With allowance for the presence of the highly significant serial correlation for the time between seizures variable, stimulation of the previous seizure using configuration 1 significantly (p=0.039) increased the mean time between seizures by 1.343. Also, the mean time between seizures in the experimental phase was 1.23 higher than in the control phase (p=0.001).

Table 4 summarizes the results for each subject.

TABLE 4

| LCL-1 | Coefficients | | | |
|---|---|---|---|---|
| 367 Clusters | PC1 | PC2 | PC3 | PC4 |
| LnSi | 0.60 | 0.02 | −0.22 | 0.77 |
| LnSd | 0.55 | −0.03 | 0.81 | −0.20 |
| LnSc | 0.58 | 0.07 | −0.54 | −0.60 |
| LnISI | −0.03 | 1.00 | 0.07 | 0.03 |
| Variance | 2.35 | 1.00 | 0.41 | 0.24 |
| % of Total | 58.7 | 25.0 | 10.3 | 5.9 |
| Cumulative % | 58.7 | 83.8 | 94.1 | 100.0 |

TABLE 4-continued

| LCL-2 | Coefficients | | | |
|---|---|---|---|---|
| 84 Clusters | PC1 | PC2 | PC3 | PC4 |
| LnSi | 0.58 | 0.16 | −0.51 | 0.62 |
| LnSd | 0.60 | −0.02 | −0.24 | −0.76 |
| LnSc | 0.55 | −0.11 | 0.81 | 0.18 |
| LnISI | −0.02 | 0.98 | −0.17 | 0.10 |
| Variance | 2.43 | 1.03 | 0.38 | 0.16 |
| % of Total | 60.7 | 25.7 | 9.6 | 4.0 |
| Cumulative % | 60.7 | 86.4 | 96.0 | 100.0 |

| LCL-3 | Coefficients | | | |
|---|---|---|---|---|
| 682 Clusters | PC1 | PC2 | PC3 | PC4 |
| LnSi | 0.56 | 0.07 | 0.73 | 0.38 |
| LnSd | 0.60 | −0.19 | −0.04 | −0.78 |
| LnSc | 0.57 | 0.01 | −0.68 | 0.47 |
| LnISI | 0.07 | 0.98 | −0.05 | −0.18 |
| Variance | 2.07 | 1.02 | 0.55 | 0.37 |
| % of Total | 51.6 | 25.5 | 13.7 | 9.2 |
| Cumulative % | 51.6 | 77.1 | 90.8 | 100.0 |

| LCL-4 | Coefficients | | | |
|---|---|---|---|---|
| 81 Clusters | PC1 | PC2 | PC3 | PC4 |
| LnSi | 0.58 | 0.01 | −0.41 | 0.70 |
| LnSd | 0.58 | −0.01 | −0.39 | −0.71 |
| LnSc | 0.56 | −0.15 | 0.81 | 0.02 |
| LnISI | 0.09 | 0.99 | 0.13 | −0.01 |
| Variance | 2.46 | 1.00 | 0.31 | 0.23 |
| % of Total | 61.6 | 25.0 | 7.6 | 5.8 |
| Cumulative % | 61.6 | 86.5 | 94.2 | 100.0 |

| RCL-1 | Coefficients | | | |
|---|---|---|---|---|
| 197 Clusters | PC1 | PC2 | PC3 | PC4 |
| LnSi | 0.60 | −0.03 | 0.23 | 0.77 |
| LnSd | 0.58 | 0.07 | 0.53 | −0.61 |
| LnSc | 0.54 | −0.20 | −0.79 | −0.20 |
| LnISI | 0.08 | 0.98 | −0.20 | 0.03 |
| Variance | 2.51 | 1.02 | 0.35 | 0.12 |
| % of Total | 62.8 | 25.4 | 8.7 | 3.1 |
| Cumulative % | 62.8 | 88.2 | 96.9 | 100.0 |

| RCL-2 | Coefficients | | | |
|---|---|---|---|---|
| 3462 Clusters | PC1 | PC2 | PC3 | PC4 |
| LnSi | 0.59 | 0.06 | 0.19 | 0.79 |
| LnSd | 0.56 | 0.02 | −0.79 | −0.23 |
| LnSc | 0.57 | 0.13 | 0.57 | −0.57 |
| LnISI | −0.12 | 0.99 | −0.07 | 0.03 |
| Variance | 2.32 | 0.98 | 0.39 | 0.30 |
| % of Total | 58.1 | 24.6 | 9.8 | 7.4 |
| Cumulative % | 58.1 | 82.7 | 92.6 | 100.0 |

| RCL-3 | Coefficients | | | |
|---|---|---|---|---|
| 159 Clusters | PC1 | PC2 | PC3 | PC4 |
| LnSi | 0.60 | 0.02 | 0.32 | 0.74 |
| LnSd | 0.59 | −0.03 | 0.46 | −0.67 |
| LnSc | 0.54 | 0.12 | −0.83 | −0.09 |
| LnISI | −0.06 | 0.99 | 0.10 | −0.03 |
| Variance | 2.52 | 1.00 | 0.35 | 0.13 |
| % of Total | 62.9 | 25.1 | 8.8 | 3.3 |
| Cumulative % | 62.9 | 88.0 | 96.7 | 100.0 |

| RCL-4 | Coefficients | | | |
|---|---|---|---|---|
| 216 Clusters | PC1 | PC2 | PC3 | PC4 |
| LnSi | 0.58 | 0.07 | 0.45 | 0.67 |
| LnSd | 0.58 | −0.05 | 0.35 | −0.73 |
| LnSc | 0.54 | −0.35 | −0.76 | 0.09 |
| LnISI | 0.19 | 0.93 | −0.30 | −0.06 |

TABLE 4-continued

| Variance | 2.48 | 1.02 | 0.28 | 0.23 |
| --- | --- | --- | --- | --- |
| % of Total | 61.9 | 25.5 | 7.0 | 5.6 |
| Cumulative % | 61.9 | 87.4 | 94.4 | 100.0 |

Table 4. Summary of the results for each subject (1-8). LCL=Local Closed-Loop; RCL=Remote Closed-Loop; SS=Seizure Severity; SZ=Total number of seizures; Stims.=: Number of Seizures stimulated; SPC=Number of stimulation parameter configurations; Variable=Dependent Variable; % Var=Percentage of variation accounted for by the final model; Sig=Significance (p) of the equation; Corr=Estimated serial correlation; Terms in model=Number of terms in final model; Stimulation Effects=Estimated stimulation effects.

Discussion

Therapeutic decisions in the management of the epilepsies rely on subjective measures of clinical seizure frequency typically gleaned from patient diaries, which are notoriously inaccurate [1, 2]. This limitation may be unavoidable or even acceptable if anti-seizure drugs are a viable option, but when alternative therapies must be considered, as in the case of pharmaco-resistant epilepsies, accurate quantification of all relevant seizure dimensions is desirable in order to attempt to increase efficacy, reduce adverse events and understand their spatio-temporal behavior over short or long time scales. Consider, for instance, brain electrical stimulation. As these results demonstrate, clinical seizure frequency alone, even if accurately measured, would be inadequate for assessment of efficacy and selection of "optimal" stimulation parameters. The effect of electrical stimulation, which as shown in this study may be beneficial or detrimental (depending among other factors on site of delivery and the parameters used), is not restricted to seizure frequency but also impacts intensity, duration and extent of spread or severity. Thus, valid assessment and optimization of any anti-seizure therapy requires quantitative analyses that include subclinical —not just clinical—events as well as statistical methods that take into account the effects of timing of stimulation and of its other parameters, circadian influences (time of day), the presence or absence of immediate and prolonged ("carry-over") stimulation effects and of their"valence" (positive or negative) and the time elapsed since the delivery of the last treatment.

The results of the analyses performed on these subjects, bring to the forefront the following observations:

1. While it is obvious that seizures can be characterized by their intensity, duration, extent of spread and rate of occurrence, these variables or dimensions have not been considered in investigations of the dynamics of epilepsy or in the assessment of therapies, due until recently to the lack of means for quantifying said dimensions. Worthwhile characterization of seizure dynamics and assessment of efficacy of therapies requires that all four dimensions be considered. Intensity, duration and extent of spread may be conflated into a single clinically useful measure, seizure severity (SS) [6], that as shown by the PCA analysis may be conveniently represented by the standardized average of their natural logarithms [$SS=\frac{1}{3}(LnSi+LnSd+LnSc)$]; interestingly this measure is identical to the logarithm of the geometric mean. Similarly, measures of seizure frequency are likely to yield valuable insight into the temporal behavior of the epilepsies. A framework that includes both measures, severity and frequency, will translate into a more valid assessment of therapeutic efficacy and in the case of electrical stimulation, allow probing of the extent to which delivery of currents to the brain—and seizures themselves—affect the timing and likelihood of occurrence of future seizures. As shown here and in previous work [4], measures of seizure severity are inter-correlated: the more intense and longer the seizure, the higher the probability of spread and generalization. Inter-correlation between measures of severity is a source of feature redundancy, that is, each measure is dependent not only on extraneous factors but also on the other measures in the set, a property that must be accounted for in the statistical analysis of any data to avoid errors in hypothesis testing.

2. That intensity, duration, spread and time between seizures may not be normally distributed (FIG. 11) must be taken into account in the selection of tests for statistical analyses. Furthermore, the influence of extraneous factors (circadian rhythm, drug taper, sleep stage, etc.) on seizure severity and recurrence may manifest itself in the form of serial correlation in seizure severity and recurrence [7, 8].

3. The multifarious nature of the effects of electrical stimulation, as performed in this trial, at both the intra- and inter-individual levels. Seizure severity and time between seizures, as measured here was significantly reduced in certain subjects, increased in others and unchanged in some. Moreover, not only were beneficial effects in severity not necessarily extensive to time elapsed between seizures, but dual effects (beneficial and detrimental) were observed in the same subject for seizure severity (Subjects LCL-2, RCL-1, 2) and for time elapsed between seizures (Subjects RCL-1, 2, 4). The effects of changes in stimulation parameters were complex and may be attributable in part to difference in brain excitability as a function of time. In subject RCL-2, one parameter configuration (143 Hz., 5.5 mA; 30 s; 100 us) increased seizure severity while other configurations (143 Hz., 8.5 mA; 30 s; 100 us and 200 Hz.; 5 mA; 30 s; 100 us) had the opposite effect.

4. The existence of effects on severity and length of time between seizures that are not only immediate but also outlast the passage of electrical currents into nervous tissue ("carry-over" effect), and that may be beneficial and/or detrimental intra- and inter-individually. It was noted that in certain subjects (LCL-2), an immediate beneficial effect on severity or frequency, may be followed by a delayed deleterious one ("rebound" phenomenon) in the same subject with the same stimulation parameters. These findings suggest that the effects of electrical stimulation on seizure severity and frequency in certain subjects may be that of a "trade-off", that is, reduction in one variable may result in an increase in the other, so the net effect even if beneficial may be difficult to detect using conventional statistical analysis tools. This underscores the importance of quantification of all seizure dimensions to fully characterize the effects of any therapy.

These results are in line with those previously reported (Table 5) [6]; differences between them are not substantive as they merely reflect the pooling of clinical and so-called sub-clinical seizures (without overt behavioral changes) which were the majority. Comparison of that study (whose analysis focused on clinical seizures) with this one motivates a plausible observation: while modest in magnitude, the reductions in mean severity may have been sufficient to prevent the evolution of sub-clinical into clinical seizures. Conventional analysis of these results would have only revealed that mean clinical seizure frequency decreased by 72% in ⅚ subject and increased by 21.2% in ⅔, possibly due to contingent electrical stimulation, observations that are accurate but incomplete and not enlightening. This study's analyses identified and quantified the contributions of the independent variables (stimulation, time of day, etc.) to the measured changes in the dependent variables (severity and frequency); as an example, the increase in seizure severity in one case (RCL3) was unrelated to stimulation; it also uncovered a detrimental "carry-over" effect and confirmed the existence of a beneficial immediate and prolonged ("carry-over") stimulation effect that had been hypothesized in a previous publication [6].

TABLE 5

| Subject | Config. No. | f (Hz) | I (mA) | Dur (s) | PW (us/ phase) | Location code | No. of clusters |
|---|---|---|---|---|---|---|---|
| LCL-1 | 1 | | | NO STIMULATION | | | 344 |
| | 4 | 50 | 10 | 1 | 200 | 2 | 5 |
| | 5 | 333 | 10 | 1 | 200 | 1 | 4 |
| | 6 | 333 | 10 | 1 | 200 | 2 | 10 |
| | 7 | 500 | 10 | 1 | 200 | 2 | 7 |
| LCL-2 | 1 | | | NO STIMULATION | | | 81 |
| | 6 | 125 | 5 | 1 | 100 | 3 | 4 |
| LCL-3 | 1 | | | NO STIMULATION | | | 666 |
| | 2 | 100 | 5 | 1 | 200 | 1 | 3 |
| | 3 | 125 | 5 | 1 | 200 | 1 | 11 |
| | 4 | 225 | 5 | 1 | 200 | 1 | 4 |
| LCL-4 | 1 | | | NO STIMULATION | | | 83 |
| | 7 | 100 | 5 | 1 | 100 | 3 | 2 |
| RCL-1 | 1 | | | NO STIMULATION | | | 169 |
| | 13 | 100 | 1.5 | 30 | 100 | 5 | 27 |
| | 18 | 142.9 | 1.5 | 30 | 100 | 5 | 1 |
| | 19 | 142.9 | 2.5 | 30 | 100 | 5 | 2 |
| RCL-2 | 1 | | | NO STIMULATION | | | 2929 |
| | 7 | 100 | 5 | 2.5 | 100 | 3 | 61 |
| | 8 | 142.9 | 5 | 2.5 | 100 | 3 | 92 |
| | 9 | 142.9 | 5 | 30 | 100 | 3 | 118 |
| | 10 | 142.9 | 5.5 | 30 | 100 | 3 | 14 |
| | 11 | 142.9 | 6 | 30 | 100 | 3 | 6 |
| | 12 | 142.9 | 6.5 | 30 | 100 | 3 | 3 |
| | 13 | 142.9 | 7 | 30 | 100 | 3 | 2 |
| | 14 | 142.9 | 8 | 30 | 100 | 3 | 1 |
| | 15 | 142.9 | 8.5 | 30 | 100 | 3 | 46 |
| | 16 | 200 | 5 | 30 | 100 | 3 | 194 |
| RCL-3 | 1 | | | NO STIMULATION | | | 168 |
| | 12 | 100 | 5 | 2.5 | 100 | 6 | 2 |
| RCL-4 | 1 | | | NO STIMULATION | | | 193 |
| | 4 | 100 | 5 | 30 | 100 | 2 | 5 |
| | 5 | 142.9 | 5 | 30 | 100 | 2 | 10 |
| | 7 | 200 | 5 | 30 | 100 | 2 | 10 |

Table 5. Number of clinical seizures/hour for each subject. Six of the eight subjects had a reduction in seizure frequency in the Experimental Phase (EP) compared to the Control Phase (CP). For all subjects pooled seizure frequency is reduced by 47.2%, from 0.052 seizures/hour to 0.027 seizures/hour.

Two inferences, at once promising and sobering may be drawn from this study: one, that contingent electrical stimulation deserves a place in the armamentarium of therapies for pharmaco-resistant seizures and the other that its apparently narrow therapeutic ratio calls for careful implementation and real-time quantification of its effects on epileptogenic brain tissue. Electrical currents may be delivered not only contingently for the purpose of abating seizures but also "prophylactically" when the beneficial "carry-over" effect (if present) begins to wane; in subjects such as LCL-2 in whom the beneficial "carry-over" gives way to a detrimental effect, analyses of ECoG recordings over a suitable time interval may allow identification of the time at which the therapeutic effect changes "direction", a necessary step for attempting to revert this trend.

While electrical stimulation was the treatment modality investigated in this study, the proposed approach and methods are applicable to any other therapeutic modality. Dose, coefficient of diffusion and type of drug and temperature and diffusivity for a thermal modality, would replace stimulation parameters in the assessment of efficacy.

Advances in the understanding of the mechanisms of action of anti-seizure therapies are unlikely to materialize unless measures of intensity, duration, extent of spread and time between seizures are adopted and analyzed with suitable (e.g., multivariate) statistical tools.

REFERENCES

All the references listed below are hereby incorporated by reference here to the extent they provide relevant information.

1. Blum D E, Eskola J, Bortz J J, Fisher R S. Patient awareness of seizures; Neurology 2000; 47:260-4

2. Hoppe C, Poepel A, Elger C E. Epilepsy: accuracy of patient seizure counts. Arch Neurol 2007; 64, 1595-99.

3. Osorio I, Frei M G, Wilkinson S B. Real-time automated detection and quantitative analysis of seizures and short-term prediction of clinical onset. Epilepsia; 1998; 39, 615-27.

4. Osorio I, Frei M G, Manly B F J, Sunderam S. An introduction to contingent (closed-loop) brain electrical stimulation for seizure blockage, to ultra-short-term clinical trials and to multidimensional statistical analysis of therapeutic efficacy. J Clin Neurophysiol 2001; 18:533-544.

5. Osorio I, Frei M G, Giftakis J, Peters T. Performance re-assessment of a real-time seizure detection algorithm on long ECoG series. Epilepsia 2002; 43:1522-35.

6. Osorio I, Frei M, Sunderam S, Bhavaraju N. Automated Seizure Abatement in Humans Using Electrical Stimulation. Ann Neurol 2005; 57:258-68

7. Lasemidis, L D, Olson L D, Savit R S, Sackellares, J C. Time dependencies in the occurrences of epileptic seizures; Epilepsy Res 1994; 17:81-94.

8. Sunderam S, Osorio I, Frei M G. Epileptic seizures are temporally interdependent under certain conditions. Epilepsy Res., 2007; 76:77-84.

9. Barkley G L, Smith B, Bergey G, Worrell G, Drazkowski J, Labar D, Duchrow R, Murro A, Smith M, Gwinn R, Fish B, Hirsch L, Morrell M. Safety and preliminary efficacy of a responsive neurostimulator; Neurology 2006 (Supp. 2) A387.

10. Fisher R S, Salanova V, Witt T, Henry T, et al. Electrical Stimulation of Anterior Nucleus of Thalamus for Treatment of Refractory Epilepsy; Epilepsies In Press.

11. Manly, B F J. *Multivariate Statistical Methods: a Primer,* 3rd Edition; Boca Raton Chapman and Hall/CRC, 2004.

12. Manly, B F J. *Statistics for Environmental Science and Management,* 2nd Edition; Boca Raton Chapman and Hall/CRC 2008.

13. Durazzo T S, Spencer S S, Duckrow R B, Novotny E J, Spencer D D, Zaveri H P. Temporal distributions of seizure occurrence from various epileptogenic regions. Neurology 2008; 70:1265-71

14. Peters T E, Bhavaraju N C, Frei M G, Osorio I. Network system seizure detection and contingent delivery of therapy; J Clin Neurophysiol 2001; 18:545-549.

15. Agnew W F, McCreery D B, eds. Neural prostheses: fundamental studies. Englewood Cliff, N.J.: Prentice Hall, 1990.

16. Lawes Agricultural Trust (2008). *GenStat* 11. VSN International, U.K.

All of the methods and systems disclosed and claimed herein can be made and executed without undue experimentation in light of the present disclosure. While the compositions and methods of this disclosure have been described in terms of particular embodiments, it will be apparent that variations may be applied to the methods and systems and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

U.S. patent application Ser. No. 12/756,065, filed Apr. 7, 2010
U.S. patent application Ser. No. 12/770,562, filed Apr. 29, 2010
U.S. patent application Ser. No. 12/896,525, filed Oct. 1, 2010
U.S. patent application Ser. No. 13/040,996, filed Mar. 4, 2011
U.S. patent application Ser. No. 13/091,033, filed Apr. 20, 2011
U.S. patent application Ser. No. 13/098,262, filed Apr. 29, 2011
U.S. Pat. No. 4,702,254
U.S. Pat. No. 4,867,164
U.S. Pat. No. 5,025,807
U.S. Pat. No. 6,961,618
U.S. Pat. No. 7,457,665

What is claimed:

1. A method of assessing an effect of a therapy on a severity of a detected epileptic seizure, comprising:
    detecting and treating a plurality of seizures in a patient;
    selecting by an internal controller of an implantable medical device an intensity associated with each of a first detected and treated seizure, a second detected and treated seizure, and a third detected and treated seizure;
    selecting by the internal controller of the implantable medical device a duration associated with each of the first detected and treated seizure, the second detected and treated seizure, and the third detected and treated seizure;
    selecting by the internal controller of the implantable medical device an extent of spread associated with each of the first detected and treated seizure, the second detected and treated seizure, and the third detected and treated seizure;
    determining by the internal controller of the implantable medical device an index of the severity associated with each of the first detected and treated seizure, the second detected and treated seizure, and the third detected and treated seizure, wherein the index of severity is determined using one or more of an autonomic index, a metabolic index, a neurologic index, a tissue stress marker, a musculoskeletal index, or an endocrine index;
    determining by the internal controller of the implantable medical device a severity associated with each of the first detected and treated seizure, the second detected and treated seizure, and the third detected and treated seizure based at least in part on the intensity associated with the corresponding detected and treated seizure, the duration associated with the corresponding detected and treated seizure, and the extent of spread associated with the corresponding detected and treated seizure, and the index of the severity associated with the corresponding detected and treated seizure;
    selecting by the internal controller of the implantable medical device one or more of:
        a parameter of the therapy for the plurality of detected and treated seizures, a parameter of a delivery of the therapy for the plurality of detected and treated seizures, a temporal factor for the plurality of detected and treated seizures, an environmental factor for the plurality of detected and treated seizures, or a patient factor for the plurality of detected and treated seizures;
    quantifying by the internal controller of the implantable medical device at least one effect of: the therapy parameter for at least one of: the first detected and treated seizure, the second detected and treated seizure, and the third detected and treated seizure; the therapy delivery parameter for at least one of: the first detected and treated seizure, the second detected and treated seizure, and the third detected and treated seizure; the temporal factor for at least one of: the first detected and treated seizure, the second detected and treated seizure, and the third detected and treated seizure; the environmental factor for at least one of: the first detected and treated seizure, the second detected and treated seizure, and the third detected and treated seizure; and the patient factor for at least one of: the first detected and treated seizure, the second detected and treated seizure, and the third detected and treated seizure on at least one of: the intensity associated with the corresponding detected and treated seizure, the duration associated with the corresponding detected and treated seizure, and the extent of spread associated with the corresponding detected and treated seizure; and
    performing an action by the implantable medical device in response to the quantification of the parameter of therapy associated with the corresponding detected and treated seizure, the parameter of the delivery of the therapy associated with the corresponding detected and treated seizure, the temporal factor associated with the corresponding detected and treated seizure, the environmental factor associated with the corresponding detected and treated seizure, or the patient factor associated with the corresponding detected and treated seizure, where the action is at least one of:
        reporting at least one effect of the therapy for at least one of: the first detected and treated seizure, the second detected and treated seizure, and the third detected and treated seizure;
        determining if the therapy effect is beneficial, neutral, or adverse the first detected and treated seizure, the second detected and treated seizure, and the third detected and treated seizure;
        providing a modification recommendation for the therapy for at least one of: the first detected and treated seizure, the second detected and treated seizure, and the third detected and treated seizure;
        or termination of the therapy for at least one of: the first detected and treated seizure, the second detected and treated seizure, and the third detected and treated seizure;
    wherein the therapy is an electrical stimulation of a cranial nerve.

2. The method of claim 1, further comprising ranking by the implantable medical device the plurality of detected and treated seizures, according to at least one of a magnitude or a direction of change.

3. The method of claim 1, further comprising logging by the implantable medical device to memory data relating to the plurality of detected and treated seizures.

4. The method of claim 1, further comprising determining: that a detected seizure was treated with any therapy, a time elapsed since a previous treatment with any therapy, a number of detected seizures since a previous treatment with any therapy, a time of day the detected seizure occurred, a time of month the detected seizure occurred, a time of year the detected seizure occurred, a type of any previous therapy, a dose of any previous therapy, a current density, a degree of tissue cooling, a degree of tissue warming, a level of consciousness, a level and type of cognitive activity, a level and type of physical activity, a state of health, a concentration of medicaments or chemicals in a tissue, or two or more of the foregoing.

5. The method of claim 1, further comprising delivering at least one additional therapy for one or more of the plurality of detected and treated seizures, where the additional therapy is selected from an electrical stimulation of a target structure of a brain, a drug, a thermal treatment of a neural structure, a cognitive therapy, or two or more thereof.

6. The method of claim 1, wherein the quantifying comprises a regression analysis.

7. The method of claim 1, further comprising determining with the implantable medical device the effect of the parameter of the therapy for each of the plurality of detected and treated seizures, the parameter of a delivery of the therapy for each of the plurality of detected and treated seizures, the temporal factor for each of the plurality of detected and treated seizures, the environmental factor for each of the plurality of detected and treated seizures, or the patient factor for each of the plurality of detected and treated seizures on: the intensity corresponding with each of the plurality of detected and treated seizures, the duration corresponding with each of the plurality of detected and treated seizures, the extent of spread corresponding with each of the plurality of detected and treated seizures is beneficial, neutral, or adverse and ranking a beneficial effect and an adverse effect.

8. An implantable medical device system, comprising:
an implantable medical device, comprising:
a data acquisition unit configured to acquire data relating each of a plurality of detected and treated seizures in a patient where the data is at least one of: an intensity of a detected and treated seizure or a severity of the detected and treated seizure, wherein the severity of the detected and treated seizure is determined based at least in part on the intensity of the detected seizure, a duration of the detected seizure, and an extent of spread of the detected and treated seizure and an index of the severity of the plurality of detected and treated seizures comprises one or more of an autonomic index, a metabolic index, a neurologic index, a tissue stress marker, a musculoskeletal index, or an endocrine index, and the data acquisition unit is further configured to acquire a therapy parameter associated with each of the plurality of detected and treated seizures, a therapy delivery parameter associated with each of the plurality of detected and treated seizures, a temporal factor associated with each of the plurality of detected and treated seizures, an environmental factor associated with each of the plurality of detected and treated seizures, or a patient factor associated with each of the plurality of detected and treated seizures;
a data quantification unit configured to quantify at least one effect of: a therapy parameter associated with each of the plurality of detected and treated seizures, a therapy delivery parameter associated with each of the plurality of detected and treated seizures, a temporal factor associated with each of the plurality of detected and treated seizures, an environmental factor associated with each of the plurality of detected and treated seizures, or a patient factor associated with each of the plurality of detected and treated seizures on: the intensity of the corresponding seizure, the severity of the corresponding seizure, the duration of the corresponding seizure, or the extent of spread for the corresponding seizure;
a therapy unit configured to administer at least one therapy to the patient, wherein the therapy is an electrical stimulation of a cranial nerve; and
an efficacy assessment unit configured to determine a magnitude of efficacy based on the quantification of the parameter of therapy associated with the corresponding detected and treated seizure, the parameter of the delivery of the therapy associated with the corresponding detected and treated seizure, the temporal factor associated with the corresponding detected and treated seizure, the environmental factor associated with the corresponding detected and treated seizure, or the patient factor associated with the corresponding detected and treated seizure, the efficacy assessment unit further configured perform and action in response to determining the magnitude of efficacy, where the action is at least one of:
report at least one effect of the therapy for at least one of: the first detected and treated seizure, the second detected and treated seizure, and the third detected and treated seizure;
determine if the therapy effect is beneficial, neutral, or adverse the first detected and treated seizure, the second detected and treated seizure, and the third detected and treated seizure;
provide a modification recommendation for the therapy for at least one of: the first detected and treated seizure, the second detected and treated seizure, and the third detected and treated seizure; or
terminate the therapy for at least one of: the first detected and treated seizure, the second detected and treated seizure, and the third detected and treated seizure.

9. The implantable medical device system of claim 8, wherein the data quantification unit comprises a regression analysis unit configured to perform a regression analysis.

10. The implantable medical device system of claim 8, further comprising at least one sensor configured to sense at least one body signal relating to the intensity of each of a plurality of detected and treated seizures, the severity of each of a plurality of detected and treated seizures, the duration of each of a plurality of detected and treated seizures, or the extent of spread of each of a plurality of detected and treated seizures.

11. The implantable medical device system of claim 8, further comprising at least one sensor configured to sense at least one signal relating to a therapy parameter associated with each of the plurality of detected and treated seizures, a therapy delivery parameter associated with each of the plurality of detected and treated seizures, a temporal factor associated with each of the plurality of detected and treated seizures, an environmental factor associated with each of the plurality of detected and treated seizures, or a patient factor associated with each of the plurality of detected and treated seizures.

12. The implantable medical device system of claim 8, further comprising an additional therapy unit configured to administer at least one additional therapy including at least one of: an electrical stimulation to a target structure of a brain of the patient; a drug to a body of the patient; a thermal therapy to a target structure of the brain, a target portion of a cranial nerve, or both of the patient; a sensory therapy to a sensory organ of the patient; or a cognitive therapy to the patient.

13. A non-transitory computer readable program storage medium containing instructions that, when executed by an implantable medical device, perform a method of assessing an efficacy of an epilepsy therapy on detected and treated seizures, the method comprising:
  selecting an intensity of a detected and treated seizure or a severity of the detected and treated seizure, wherein the severity is determined based at least in part on the intensity of the detected and treated seizure, a duration of the detected and treated seizure, and an extent of spread of the detected and treated seizure and an index of the severity of the detected seizure, which comprises one or more of an autonomic index, a metabolic index, a neurologic index, a tissue stress marker, a musculoskeletal index, or an endocrine index;
  selecting a parameter of the therapy associated with each detected and treated seizure, a parameter of a delivery of the therapy associated with each detected and treated seizure, a temporal factor associated with each detected and treated seizure, an environmental factor associated with each detected and treated seizure, or a patient factor associated with each detected and treated seizure;
  quantifying at least one effect of the parameter of the therapy associated with each detected and treated seizure, the parameter of a delivery of the therapy associated with each detected and treated seizure, the temporal factor associated with each detected and treated seizure, the environmental factor associated with each detected and treated seizure, or the patient factor associated with each detected and treated seizure on: the intensity of the corresponding seizure, the severity of the corresponding seizure, the duration of the corresponding seizure, or the extent of spread for the corresponding seizure; and
    determining a magnitude of efficacy based on the quantification of the parameter of therapy associated with the corresponding detected and treated seizure, the parameter of the delivery of the therapy associated with the corresponding detected and treated seizure, the temporal factor associated with the corresponding detected and treated seizure, the environmental factor associated with the corresponding detected and treated seizure, or the patient factor associated with the corresponding detected and treated seizure; and
    performing an action in response to determining the magnitude of efficacy, where the action is at least one of:
  report at least one effect of the therapy for at least one of: the first detected and treated seizure, the second detected and treated seizure and the third detected and treated seizure;
  determine if the therapy effect is beneficial, neutral, or adverse the first detected and treated seizure the second detected and treated seizure, and the third detected and treated seizure;
  provide a modification recommendation for the therapy for at least one of: the first detected and treated seizure, the second detected and treated seizure, and the third detected and treated seizure; or
  terminate the therapy for at least one of: the first detected and treated seizure, the second detected and treated seizure, and the third detected and treated seizure,
  wherein the therapy is an electrical stimulation of a cranial nerve.

14. The non-transitory computer readable program storage medium of claim 13, wherein the method further comprises ranking the detected and treated seizures, according to at least one of a magnitude or a direction of change.

15. The non-transitory computer readable program storage medium of claim 13, the method further comprising determining a frequency of the detected and treated seizures, an interval(s) between detected and treated seizures, or an adverse effect of a therapy on detected and treated seizures.

16. The non-transitory computer readable program storage medium of claim 13, the method further comprising determining: that a detected seizure was treated with any therapy, a time elapsed since a previous treatment with any therapy, a number of detected seizures since a previous treatment of a previously detected seizure with any therapy, a time of day the detected seizure occurred, a time of month the detected seizure occurred, a time of year the detected seizure occurred, a type of any previous therapy of detected seizures, a dose of any previous therapy of detected seizures, a current density, a degree of tissue cooling, a degree of tissue warming, a level of consciousness, a level and type of cognitive activity, a level an type of physical activity, a state of health, a concentration of medicaments or chemicals in a tissue, or two or more of the foregoing.

17. The non-transitory computer readable program storage medium of claim 13, the method further comprising delivering at least one additional therapy for detected and treated seizures where the additional therapy is selected from an electrical stimulation of a target structure of a brain, a drug, a thermal treatment of a target portion of a neural structure, or a cognitive therapy.

18. The non-transitory computer readable program storage medium of claim 13, wherein the quantifying comprises a regression analysis.

19. The non-transitory computer readable program storage medium of claim 13, further comprising at least one of modifying and initiating a therapy based on the determination of the magnitude of efficacy.

* * * * *